US008053634B2

(12) United States Patent
Tanaka et al.

(10) Patent No.: US 8,053,634 B2
(45) Date of Patent: Nov. 8, 2011

(54) STABILIZATION AND BLUEING OF ANTHOCYANIN PIGMENTS USING GENE ENCODING AROMATIC ACYLTRANSFERASE CAPABLE OF TRANSFERRING AN AROMATIC ACYL GROUP TO THE 3'-POSITION OF ANTHOCYANIN

(75) Inventors: Yoshikazu Tanaka, Otsu (JP); Yukihisa Katsumoto, Osaka (JP); Masako Mizutani, Kyoto (JP); Yuko Fukui, Takatsuki (JP); Junichi Togami, Takatsuki (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 1212 days.

(21) Appl. No.: 11/665,741

(22) PCT Filed: Oct. 28, 2005

(86) PCT No.: PCT/JP2005/020251
§ 371 (c)(1),
(2), (4) Date: Apr. 27, 2007

(87) PCT Pub. No.: WO2006/046780
PCT Pub. Date: May 4, 2006

(65) Prior Publication Data
US 2011/0055963 A1 Mar. 3, 2011

(30) Foreign Application Priority Data
Oct. 29, 2004 (JP) .................................. 2004-315733

(51) Int. Cl.
*C12N 15/82* (2006.01)
*C12N 5/04* (2006.01)
*C12N 5/10* (2006.01)
*C12N 15/29* (2006.01)
*C12N 15/54* (2006.01)
*A01H 5/00* (2006.01)
*A01H 5/02* (2006.01)
*C12P 21/02* (2006.01)

(52) U.S. Cl. .... 800/282; 435/70.1; 435/193; 435/320.1; 536/23.2; 536/23.6; 530/370

(58) Field of Classification Search .................. None
See application file for complete search history.

(56) References Cited

FOREIGN PATENT DOCUMENTS

| EP | 0810287 A1 * | 2/1996 |
| EP | 0 180 287 A1 | 12/1997 |
| EP | 0 810 287 A1 | 12/1997 |
| EP | 1652916 | 5/2006 |
| JP | 9-70290 | 3/1997 |
| JP | 2003528603 | 9/2003 |
| WO | WO 9602550 A1 * | 2/1996 |
| WO | WO 01/72984 A1 | 10/2001 |
| WO | WO 2005/017147 A1 | 2/2005 |

OTHER PUBLICATIONS

Fujiwara et al. "cDNA cloning, gene expressoin and subcellular localization of anthocyanin 5-aromatic acyltransferase from *Gentiana triflora*" The Plant J. (1998) 16(4) pp. 421-431.*
Fukuchi-Mizutani et al. "Biochemical and Molecular Characterization of a Novel UDP-Glucose: Anthocyanin 3'-O-Glucosyltransferase, a Key Enzyme for Blue Anthocyanin Biosynthesis, from Gentian", (2003) Plant Physio. 132 pp. 1652-1663.*
H. Fujiwara et al., "cDNA cloning, gene expression and subcellular localization of anthocyanin 5-aromatic acyltransferase from *Gentiana triflora*," The Plant Journal, 1998, vol. 16, No. 4, pp. 421-431.
G. Forkmann et al., "Metabolic engineering and applications of flavonoids," Plant Biotechnology, Apr. 2001, vol. 12, No. 2, pp. 155-160.
T. Nakayama et al., "Anthocyanin acyltransferases: specificities, mechanism, phylogenetics, and applications," Journal of Molecular Catalysis B: Enzymatic, 2003, vol. 23, pp. 117-132.
M. Fukuchi-Mizutani et al., "Biochemical and Molecular Characterization of a Novel UDP-Glucose: Anthocyanin 3'-O-Glucosyltransferase, a Key Enzyme for Blue Anthocyanin Biosynthesis, from Gentian," Plant Physiology, Jul. 2003, vol. 32, pp. 1652-1663.
K. Yonekura-Sakakibara et al., "Molecular and Biochemical Characterization of a Novel Hydroxycinnamoyl-CoA: Anthocyanin 3-O-Glucoside-6-O-Acyltransferase from *Perilla frutescens*," Plant Cell Physiology, 2000, vol. 4, No. 4, pp. 495-502.
H. Fujiwara et al., "Anthocyanin 5-aromatic acyltransferase from *Gentiana triflora* Purification, characterization and its role in anthocyanin biosynthesis," European Journal of Biochemistry, Oct. 1997; vol. 249, No. 1, pp. 45-51.
International Search Report mailed Jan. 17, 2006 for International PCT Application No. PCT/JP2005/02051 filed Oct. 28, 2005.
Brouillard et al., "Flavonoids and flower colour," in The Flavonoids, Advances in Research Since 1986, edited by J.B. Harborne, 1$^{st}$ ed., pp. 565-587 (1993), Chapman & Hall/CRC, London.
Holton et al., "Genetics and Biochemistry of Anthocyanin Biosynthesis," The Plant Cell, Vo. 7, pp. 1071-1083 (1995).
N. Saito, Tanpakusitu Kakusan Kouso (Proteins, Nucleic Acids, Enzymes), vol. 47, No. 3, pp. 202-209 (2002) [In Japanese].
G. Forkmann, "Flavonoids as Flower Pigments: The Formation of the Natural Spectrum and its Extension by Genetic Engineering," Plant Breeding, vol. 106, pp. 1-26 (1991).
Tanaka et al., "Manipulation of Flower Colour by Genetic Engineering," In Sigh RP & Jaiwal PK (ed.) Plant Genetic Engineering, vol. 1, Applications and Limitations, pp. 361-385, (2003), SCI Tech Publishing, Houston.

(Continued)

*Primary Examiner* — David T Fox
*Assistant Examiner* — Paul Roath
(74) *Attorney, Agent, or Firm* — Drinker Biddle & Reath LLP

(57) ABSTRACT

A method of acylating the 3' position of anthocyanin using an enzyme that transfers an aromatic acyl group to a sugar at the 3' position of anthocyanin or a gene encoding the enzyme.

8 Claims, 6 Drawing Sheets

OTHER PUBLICATIONS

Honda et al., "Recent Progress in the Chemistry of Polyacylated Anthocyanins as Flower Color Pigments," Heterocycles, vol. 56, pp. 633-692 (2002).

Goto et al., "Structure of Cinerarin, A Tetra-Acylated Anthocyanin Isolated from the Blue Garden Cineraria, *Senecia cruentus*," Tetrahedron Letters, vol. 25, No. 52, pp. 6021-6024 (1984).

Dangles et al., "Anthocyanin Intramolecular Copigment Effect," Phytochemistry, vol. 34, No. 1, pp. 119-124 (1993).

Yoshida, "Intramolecular Stacking Conformation of Gentiodelphin, a Diacylated Anthocyanin from *Gentiana Makinoi*," Tetrahedron, vol. 48, No. 21, pp. 4313-4326 (1992).

Yoshida et al., "Contribution of each caffeoyl residue of the pigment molecule of gentiodelphin to blue color development," Phytochemistry, vol. 54, pp. 85-92 (2002).

Goto et al., "Structure and Molecular Stacking of Anthocyanins—Flower Color Variation," Agnew. Chem. Int. Ed. Engl. vol. 30, pp. 17-33 (1991).

Kamsteeg et al., "Identification, Properties and Genetic Control of Hydroxycinnamoyl-coenzyme A: Anthocyanidin 3-rhamnosyl (1→6) glucoside, 4-hydroxycinnamoyl Transfersae Isolated from Petals of *Silene dioica*," Biochem. Physiol. Pflanzen vol. 175, pp. 403-411 (1980).

Teusch et al., "Genetic Control of Hydroxycinnamoyl-Coenzyme A: Anthocyanidin 3-Glycoside-Hydroxycinnamoyltransferase from Petals of *Manhiola Incana*," Phytochemistry, vol. 26, No. 4., pp. 991-994 (1987).

Office Action from the Australian Patent Office in Australian Application No. 2005297801, mailing date Jun. 25, 2010, 2 pages.

Tanaka Y et al., "*Recent Progress in Flower Colour Modification by Biotechnology*", International Journal of Molecular Science, 2009, 10, 5350-5369.

Database UniProt [Online] Oct. 25, 2004, "SubName: Full=Hydroxycinnamoyl-CoA: anthocyanin 5-glucoside-6-0-hydroxcinnamoyltransferase;" XP002549174 retrieved from EBI accession No. UNIPROT: Q65YR4.

Database UniProt [Online] May 1, 1999, "RecName: Full=Anthocyanin 5-aromatic acyltransferase; Short=5AT; EC=<A HREF=http://srs.ebi.ac.uk/srsbin/cgi-bin/wgetz?[enzyme-ECNumber: 2.3.1.153]+-e> 2.3.1.153</A>;" XP002549175 retrieved from EBI accession No. UNIPROT: Q9ZWR8.

Database Geneseq [Online] Feb. 6, 1997, "Aromatic acyl transferase of *Gentiana triflora* var. *japonica*," XP002549176 retrieved from EBI accession No. GSP: AAW04722.

Nakayama et al., "Anthocyanin acyltransferases: specificities, mechanism, phylogenetics, and applications,"; *Journal of Molecular Catalysis, B. Enzymatic*, Elsevier, Amsterdam, NL, vol. 23, No. 2-6, Sep. 1, 2003, pp. 117-132, XP002995251, ISSN: 1381-1177.

European Search Report mailed Oct. 23, 2009 in European Application No. 05800037.3.

* cited by examiner

Fig. 2
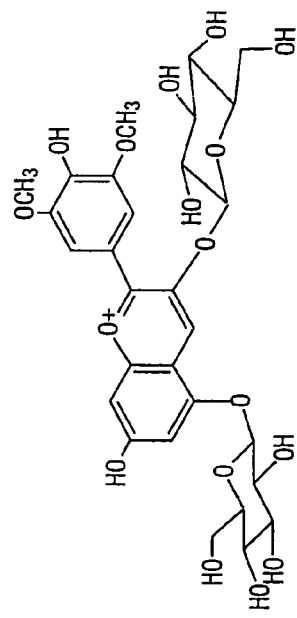
MALVIDIN 3,5-DIGLUCOSIDE (MAL 3G-5G)
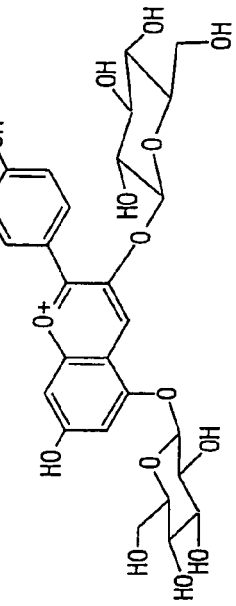
PELARGONIDIN 3,5-DIGLUCOSIDE (PEL 3G-5G)
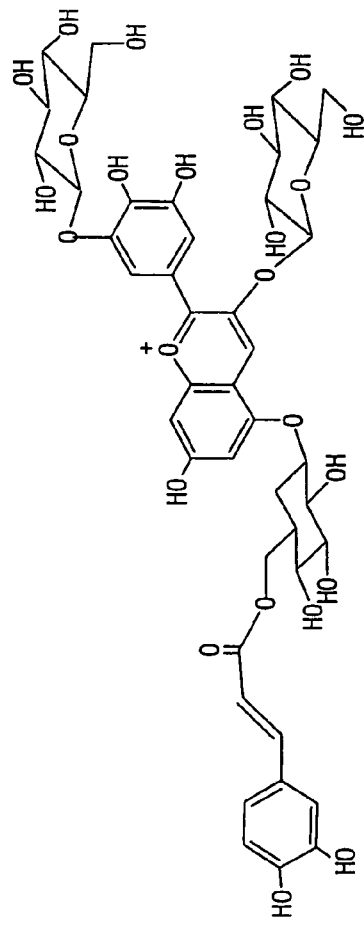
DELPHINIDIN 3-GLUCOSYL-5-CAFFEOYLGLUCOSYL-3'-GLUCOSIDE
(DEL 3G-5CafG-3'G)
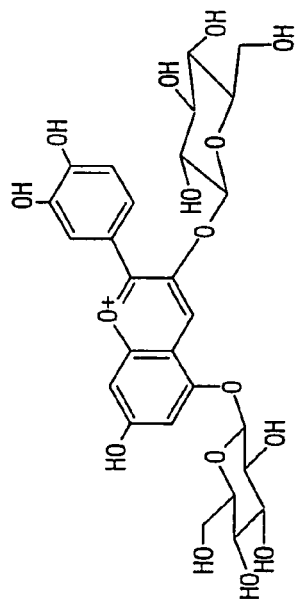
CYANIDIN 3,5-DIGLUCOSIDE (CYA 3G-5G)

(A)

(B)

50 μM DEL 3G-5G-3'G

| TIME (MINUTES) | 5,3'Caf (μM) | 5Caf (μM) | 3'Caf (μM) | triG (μM) |
|---|---|---|---|---|
| 2.5 | 1.65 | 13.05 | 0.00 | 35.3 |
| 5.0 | 3.90 | 17.40 | 0.00 | 28.7 |
| 10.0 | 7.30 | 18.15 | 0.00 | 24.6 |
| 20.0 | 11.70 | 16.20 | 0.00 | 22.1 |

(A)

(B)

100 μM  DEL 3G-5G-3'G

| TIME (MINUTES) | 5,3'Caf (μM) | 5Caf (μM) | 3'Caf (μM) | triG (μM) |
|---|---|---|---|---|
| 2.5 | 1.70 | 21.80 | 0.00 | 76.5 |
| 5.0 | 3.50 | 30.10 | 0.00 | 66.4 |
| 10.0 | 6.80 | 35.60 | 0.00 | 57.6 |
| 20.0 | 11.80 | 39.60 | 0.00 | 48.6 |

(A)

(B)

200 μM DEL 3G-5G-3'G

| TIME (MINUTES) | 5,3'Caf (μM) | 5Caf (μM) | 3'Caf (μM) | triG (μM) |
|---|---|---|---|---|
| 2.5 | 1.60 | 31.20 | 0.00 | 167.2 |
| 5.0 | 3.00 | 44.40 | 0.00 | 152.6 |
| 10.0 | 7.00 | 60.60 | 0.20 | 132.2 |
| 20.0 | 11.60 | 70.00 | 0.60 | 117.8 |

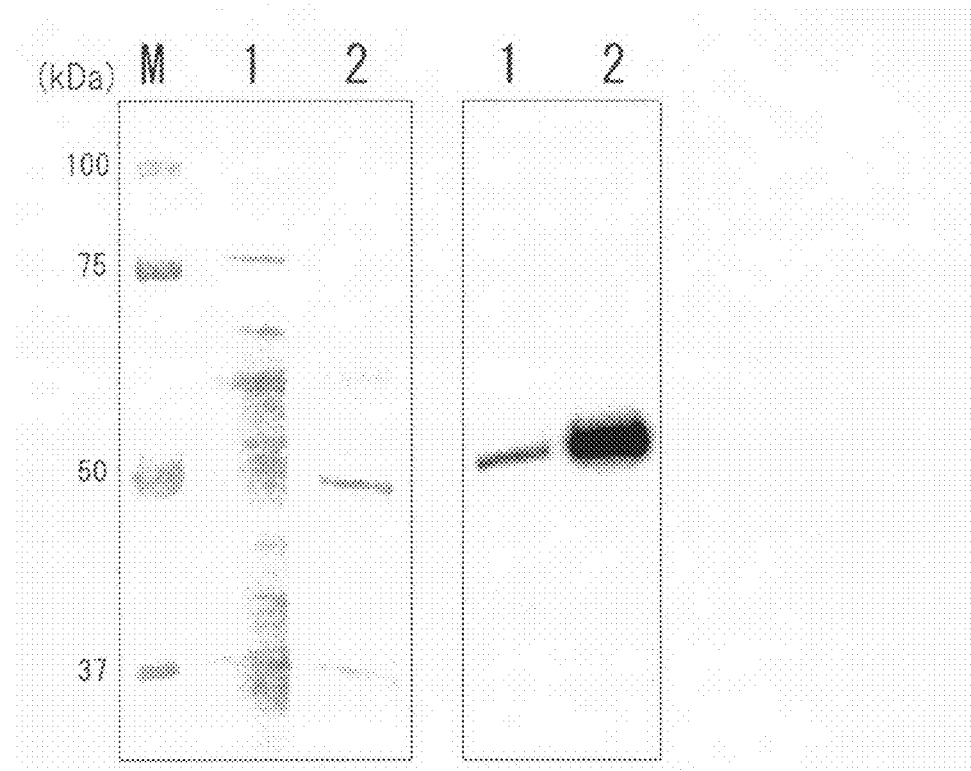
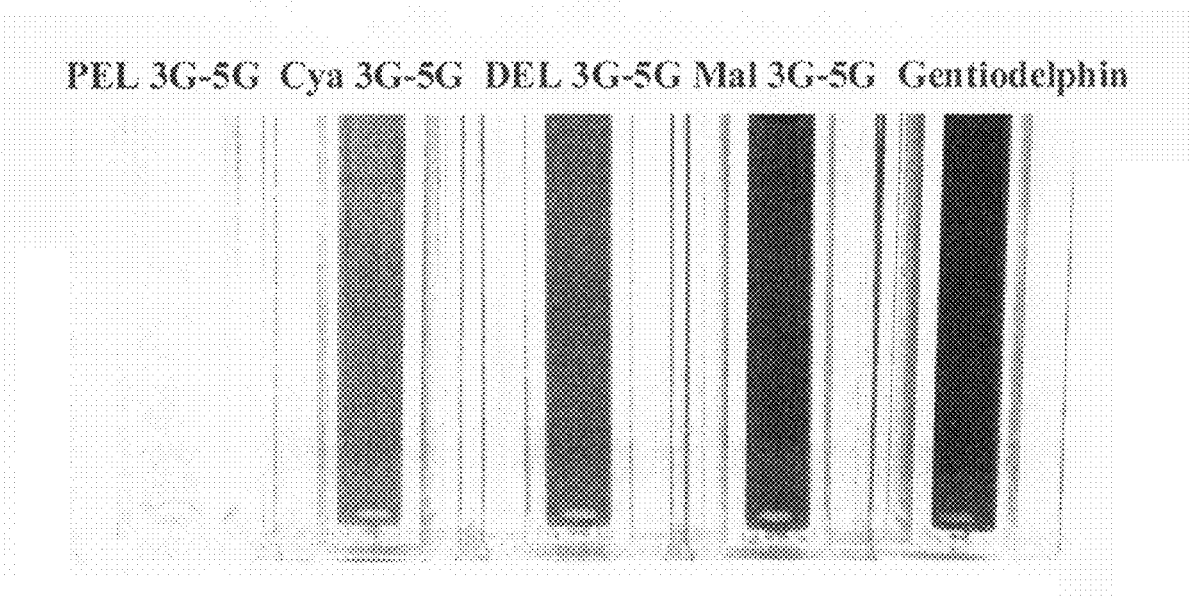

STABILIZATION AND BLUEING OF ANTHOCYANIN PIGMENTS USING GENE ENCODING AROMATIC ACYLTRANSFERASE CAPABLE OF TRANSFERRING AN AROMATIC ACYL GROUP TO THE 3'-POSITION OF ANTHOCYANIN

CROSS REFERENCE TO RELATED APPLICATIONS

This application is the National Stage of International Application No. PCT/JP2005/020251 filed Oct. 28, 2005, and claims benefit of Japanese Application No. 2004-315733 filed Oct. 29, 2004, which are incorporated herein in their entirety.

REFERENCE TO A SEQUENCE LISTING

The instant application contains a Sequence Listing which has been submitted in ASCII format via EFS-Web and is hereby incorporated by reference in its entirety. Said ASCII copy, created on Oct. 25, 2010, is named 241601US.txt and is 22,207 bytes in size.

FIELD OF THE INVENTION

The present invention relates to a method of altering anthocyanin bluer and more stable using an enzyme that transfers an aromatic acyl group to the 3'-position of anthocyanin or a gene encoding said enzyme, and can be applied to the alteration and stabilization of anthocyanin pigments and to the alteration and stabilization of flower color. More specifically, it relates to a method of making the color of flowers blue and stabilizing it using an aromatic acyltransferase that transfers an aromatic acyl group to the 3'-position of anthocyanin derived from plants including *Gentiana triflora* var. *japonica* or a cDNA encoding said enzyme.

The present invention also relates to a method of altering anthocyanin bluer and more stable using a single enzyme that transfers aromatic acyl groups to sugars at multiple positions of anthocyanin or gene encoding said enzyme, and can be applied to the alteration and stabilization of anthocyanin pigments and to the alteration and stabilization of flower color.

BACKGROUND OF THE INVENTION

The flower industry strives to develop new and different varieties of flowers. An effective way to create such novel varieties is the manipulation of flower color where classical breeding techniques have been used to produce a wide range of colors for most of the commercial varieties. This approach has been limited, however, by the constraints of a particular species' gene pool and for this reason it is rare for a single species to have the full spectrum of colored varieties.

Flower color is predominantly due to two types of pigments: flavonoids and carotenoids. Flavonoids mainly contribute a wide range of color from yellow to red to blue, whereas carotenoids mainly contribute color tones such as orange or yellow. The flavonoids which are a major contribution to flower color are a class of compounds called anthocyanins. The chromophoric group of anthocyanins is anthocyanidins, and as major anthocyanidins, there are known pelargonidin, cyanidin and delphinidin. Plants are known to have a wide variety of anthocyanins, and the diversity thereof is one of the causes of the diversity of flower colors. Structures of hundreds of anthocyanins have already been determined, and the hydroxyl group at the 3 position of most anthocyanins has been modified with sugars (Harbone, in The Flavonoids: 565, 1986).

The biosynthetic pathway for anthocyanins is common among flowering plants up to the biosynthesis of the 3-glucosides (Holton et al., Plant Cell 7: 1071, 1995), and subsequently they undergo various modifications such as glycosylation, acylation and methylation in species- and variety-specific manners. Such differences in modification patterns in varieties are one of the reason for diversities in anthocyanins, i.e. diversities in flower colors. Generally the more aromatic acyl groups modify anthocyanins, the more stabilized and bluer anthocyanins become (Harbone, in the Flavonoids: 565, 1986; Norio Saito, TANPAKUSITU KAKUSAN KOUSO (Proteins, Nucleic Acids, Enzymes) 47: 202, 2002). Furthermore, flower color may be affected by the formation of metal complex of anthocyanins, the copigment effect by flavonoid compounds such as flavonol and flavone, and pH of vacuoles in which anthocyanins are localized (Forkmann, Plant Breeding 106: 1, 1991).

Biosynthesis of flavonoids including anthocyanidin has been extensively studied. All the genes for enzymes involved in anthocyanin biosynthesis have been cloned, and genes for the transcription factors therefor have also been obtained. Therefore, the artificially modification of the expression of these genes can alter the structure and the amount of flavonoids accumulated in flowers, and thereby can change flower color. There are some reports on the modification of anthocyanin structures and flower color by a molecular biological technique and gene transformation into plants (Forkmann G. & Martens S. (2001), Curr. Opin. Biotechnology, 12: 155-160; Tanaka Y. & Mason J. (2003), In: Singh R P & Jaiwal P K (ed.) Plant genetic engineering, pp. 361-385, SCI tech publishing, Houston).

One possible method for making flower color blue is to increase the number of hydroxyl groups of B ring of anthocyanin. An enzyme that catalyzes a reaction of hydroxylating the 3' position of anthocyanin (flavonoid 3'-hydroxylase: F3'H) and an enzyme that catalyzes a reaction of hydroxylating the 3' and the 5' position of anthocyanin (flavonoid 3',5'-hydroxylase: F3'5'H) are important in altering flower color. In general, pelargonidin (one hydroxyl group in B ring) is contained in orange- to red-colored flowers, cyanidin (two hydroxyl groups in B ring) is contained in red- to magenta-colored flowers, and delphinidin (three hydroxyl groups in B ring) is contained in purple- to blue-colored flowers. In most cases, plant species that do not have purple- to blue-colored varieties often lack the ability to produce delphinidin, and are represented by roses, chrysanthemums and carnations.

For these plants, the creation of purple- to blue-colored varieties by biotechnology has long attracted attention. In fact, by expressing the F3'5'H gene essential for the production of delphinidin, carnations whose flower color is blue purple were produced (Tanaka Y. & Mason J. (2003), In: Singh R P & Jaiwal P K (ed.) Plant genetic engineering, pp. 361-385, SCI tech publishing, Houston), and it became possible to produce delphinidin in flower petals, but the flower color has not been fully blue yet. Thus, in order to make flower color sheer blue, the introduction of the F3'5'H gene alone is not sufficient, and further contrivances may be required.

Actually anthocyanins contained in blue flowers are often modified with aromatic acyl groups via sugars (Honda & Saito, Heterocycles 56: 633 (2002)). Thus, one possible method of making flower color blue is to modify anthocyanins with aromatic acyl groups such as caffeoyl groups, coumaroyl groups and sinapoyl groups (Tanaka Y. & Mason J.

(2003), In: Singh R P & Jaiwal P K (ed.) Plant genetic engineering, pp. 361-385, SCI tech publishing, Houston).

Generally, anthocyanin is slightly reddened by glycosylation, and the addition of aromatic acyl groups via sugars makes the color of anthocyanin blue (Forkmann, Plant Breeding 106: 1, 1991). Also, anthocyanin is a compound unstable in neutral solutions, and the stability is enhanced by modification with sugars or acyl groups (Forkmann, Plant Breeding 106: 1, 1991). An experiment using anthocyanins from morning glories (Pharbitis nil) revealed that acylated anthocyanins to which an aromatic acyl group such as, for example, coumaric or caffeic acid was bound showed a hypsochromic shift (Dangle et al., Phytochemistry 34: 1119, 1993).

As for anthocyanins acylated with aromatic acyl groups, many isolation examples from nature have been reported including awobanin (Goto and Kondo, Angew. Chem. Int. Ed. Engl. 30: 17, 1991) derived from Commelina communis (Honda & Saito, Heterocycles 56: 633 (2002)). For example, anthocyanins from blue flowers have multiple aromatic acyl groups as represented by cinerarin (derived from cineraria), gentiodelphin (derived from *Gentiana triflora*), heavenly blue anthocyanin (derived from Pharbitis nil), ternatin (derived from Clitoria ternatea) and lobelinin (derived from Lobelia).

Cinerarin (Goto et al., Tetrahedron 25: 6021, 1984) derived from cineraria (Senecio cruentus) has one aliphatic acyl group and three aromatic acyl groups, and these aromatic acyl groups are reported to contribute to the stabilization of pigments in neutral aqueous solutions (Goto et al., Tetrahedron 25: 6021, 1984). Gentiodelphin (DEL 3G-5CafG-3' CafG) which is a major pigment of *Gentiana triflora* petals has a delphinidin 3-glycoside as the basic backbone, and two side chains comprising one glucose molecule and one caffeic acid molecule on the hydroxyl groups at the 5 position and the 3' position. It is reported that the side chains at the 5 and 3' position comprised of sugar-acyl group contributed to a sandwich-type of intra-molecular stacking, resulting in the stabilization of pigments in aqueous solutions (Yoshida et al., Tetrahedron 48: 4313, 1992). Furthermore, it has been confirmed that among the two side chains of sugar-acyl group, the glucosylacyl group at the 3' position rather than the 5 position contributes more strongly to the stabilization and blueing of pigments (Yoshida et al., Phytochemistry 54: 85, 2000).

The aromatic acyl transfer reaction was first demonstrated in Silene (Kamsteeg et al., Biochem. Physiol. Pflanzen 175: 403, 1980), a plant of the family Caryophyllaceae, in 1980, and a similar aromatic acyl transferase activity was also found in the solubilized enzyme fraction of Matthiola as well (Teusch et al., Phytochemistry 26: 991, 1986). Subsequently, an anthocyanin 5-aromatic acyltransferase (hereinafter 5AT) that transfers aromatic acyl groups such as caffeic acid and coumaric acid to sugars at the 5 position of anthocyanins was isolated from *Gentiana triflora* (Fujiwara et al., Eur. J. Biochem. 249, 45, 1997), and based on the internal amino acid sequences of the purified enzyme, cDNA that codes for 5AT of *Gentiana triflora* was isolated (Fujiwara et al., Plant J., 16, 421, 1998).

Based on this gene, a homolog was isolated from Torenia (WO 2005/017147), and furthermore based on the amino acid sequence conserved between these enzymes, a *Perilla* cDNA coding for the enzyme (3AT) that transfers aromatic acyl groups to the sugar at the 3 position of anthocyanins was isolated (Yonekura-Sakibara et al., Plant Cell Physiol 41: 495, 2000). Using the *Perilla* 3AT gene, the 3AT gene was cloned from lavender of the same family Labiatae (WO 1996/25500).

An enzyme gene that transfers an acyl group to anthocyanidin-3-rutinoside has been obtained from petunia (National Publication of Translated Version (Kohyo) No. 2003-528603). When the *Perilla* 3AT gene or the torenia 5AT gene was introduced into roses, anthocyanin in which aromatic acyl groups were added to the 3 position or the 5 position was formed in petals, but it failed to significantly alter flower color blue, and the maximum absorption spectra just shifted to the long wavelength by about 1-2 nm.

The reason for this, as reported by Yoshida et al. (Yoshida et al., Tetrahedron 48: 4313, 1992), it was thought that acylation of A ring or C ring such as the 3 or 5 position is not fully effective, and that acylation at the 3' position is necessary for blueing and stabilization of an anthocyanin, and more preferably acylation at multiple positions including the 3' position is necessary. Since there is in fact anthocyanins containing an aromatic acyl group attached to a sugar at the 3' position, the presence of an enzyme (3' AT) that catalyzes a reaction of transferring an aromatic acyl group to a sugar at the 3' position may be postulated. However, there is no report on a measurement for 3' AT reaction and no 3' AT enzyme or a gene encoding for a 3' AT has been isolated so far.

All acyltransferases reported so far act on the 3 position or the 5 position of anthocyanin, and the site specificity of the reaction has been reported to be high (Fujiwara et al., Plant J., 16, 421, 1998; Yonekura-Sakibara et al., Plant Cell Physiol 41: 495, 2000). Therefore, the acylation at the 3' position using a known aromatic acyltransferase was thought to be impossible. There have been no report for an aromatic acyltransferase that have an activity of transferring aromatic acyl groups to multiple positions of anthocyanins. Thus, with the level of conventional technology, it was impossible, for example, to create a recombinant plant and transfer aromatic acyl groups to sugars at the 3' position or multiple positions including the 3' position of anthocyanin. That is, it was impossible to add aromatic acyl groups to sugars at the 3' position or multiple positions including the 3' position of an anthocyanin in order to make a bluer and more stable anthocyanin, and to make bluer and more stable flower color.

Patent document 1: WO 1996/25500
Patent document 2: WO 2005/017147
Patent document 3: National Publication of Translated Version (Kohyo) No. 2003-528603
Non-patent document 1: Harbone, in The Flavonoids: 565, 1986
Non-patent document 2: Holton et al., Plant Cell 7: 1071, 1995
Non-patent document 3: Harbone, in The Flavonoids: 565, 1986
Non-patent document 4: Norio Saito, TANPAKUSITU KAKUSAN KOUSO (Proteins, Nucleic Acids, Enzymes) 47: 202, 2002
Non-patent document 5: Forkmann, Plant Breeding 106: 1, 1991
Non-patent document 6: Forkmann G. & Martens S. (2001), Curr. Opin. Biotechnology, 12: 155-160
Non-patent document 7: Tanaka Y. & Mason J. (2003), In: Singh R P & Jaiwal P K (ed.) Plant genetic engineering, pp. 361-385, SCI tech publishing, Houston
Non-patent document 8: Honda & Saito, Heterocycles 56: 633 (2002)
Non-patent document 9: Forkmann, Plant Breeding 106: 1, 1991
Non-patent document 10: Dangle et al., Phytochemistry 34: 1119, 1993
Non-patent document 11: Goto et al., Tetrahedron 25: 6021, 1984

Non-patent document 12: Yoshida et al., Tetrahedron 48: 4313, 1992
Non-patent document 13: Yoshida et al., Phytochemistry 54: 85, 2000
Non-patent document 14: Goto and Kondo, Angew. Chem. Int. Ed. Engl. 30: 17, 1991
Non-patent document 15: Kamsteeg et al., Biochem. Physiol. Pflanzen 175: 403, 1980
Non-patent document 16: Teusch et al., Phytochemistry 26: 991, 1986
Non-patent document 17: Fujiwara et al., Eur. J. Biochem. 249, 45, 1997
Non-patent document 18: Fujiwara et al., Plant J., 16, 421, 1998
Non-patent document 19: Yonekura-Sakakibara et al., Plant Cell Physiol 41: 495, 2000

SUMMARY OF THE INVENTION

As described in the above report by Yoshida et al., the aromatic acyl groups of anthocyanin contribute to the stabilization and blueing of anthocyanin, and specifically the sugar-acyl group side chain at the 3' position contributes more strongly than that at the 5 position. It is also believed that the sugar-acyl group side chain at multiple positions including the 3' position make anthocyanins bluer and more stable. Thus, by using an enzyme that transfers an aromatic acyl group to the 3' position of anthocyanin or multiple positions including the 3' position, or a gene encoding said enzyme, it seems to be possible to artificially modify anthocyanins and alter anthocyanins to more stable compounds, or to increase bluish hue of anthocyanins.

As described above, the transfer of aromatic acyl groups to the 3' position is very effective for the stabilization and blueing of anthocyanins. For that purpose, an aromatic acyltransferase that transfers aromatic acyl groups to the 3' position of anthocyanin or a gene encoding the enzyme is essential. The present inventors have investigated in detail the enzymatic properties of the anthocyanin 5-aromatic acyltransferase isolated from *Gentiana triflora*, and demonstrated that the 5-aromatic acyltransferase of *Gentiana triflora* also have an activity of 3'-acyl transfer. Thus, we clarified that, in spite of a single enzyme, the enzyme catalyzes the aromatic acyltransferring reactions to sugars at both of the 5 and the 3' positions of anthocyanins.

Thus, the present invention provides a method of making a bluer and more stable anthocyanin by adding an aromatic acyl group to the 3' position of anthocyanin. It also provides a method of making flower color bluer and more stable by introducing and expressing a gene encoding an aromatic acyltransferase into plants.

Thus, the present invention (1) provides a method of acylating the 3' position of anthocyanins using an enzyme that transfers an aromatic acyl group to a sugar at the 3' position of anthocyanin or a gene encoding the enzyme.

(2) The present invention also provides a method of stabilizing anthocyanins by using an enzyme that transfers an aromatic acyl group to a sugar at the 3' position of anthocyanin or a gene encoding the enzyme.

(3) The present invention also provides a method of blueing anthocyanins by using an enzyme that transfers an aromatic acyl group to a sugar at the 3' position of anthocyanin or a gene encoding the enzyme.

(4) The present invention further provides a method of acylating a pigment of interest by expressing a gene encoding an aromatic acyltransferase that transfers an aromatic acyl group to the 3' position of anthocyanin in plants.

(5) The present invention further provides a method of stabilizing a pigment of interest by introducing a gene encoding an aromatic acyltransferase that transfers an aromatic acyl group to the 3' position of anthocyanin, and acylating the pigment of interest in plants.

(6) The present invention also provides a method of blueing a pigment of interest by introducing a gene encoding an aromatic acyltransferase that transfers an aromatic acyl group to the 3' position of anthocyanin, and acylating the pigment of interest in plants.

(7) The present invention further provides a plant obtained by a method described in any of the above (4)-(6), a vegetative propagation product or a seed of a plant, or a progeny plant of a plant, a vegetative propagation product or a seed of a plant having properties identical to those of a plant.

(8) The present invention also provides a method of adding aromatic acyl groups to sugars at multiple positions of an anthocyanin, which comprises using a single enzyme that transfers aromatic acyl groups to sugars at multiple positions of an anthocyanin or a gene encoding the enzyme.

(9) The present invention further provides a method of stabilizing anthocyanin, which comprises using a single enzyme that transfers aromatic acyl groups to sugars at multiple positions of an anthocyanin or a gene encoding the enzyme.

(10) The present invention further provides a method of blueing anthocyanin, which comprises using a single enzyme that transfers aromatic acyl groups to sugars at a multiple positions of an anthocyanin or a gene encoding the enzyme.

(11) The present invention further provides a method according to any of the above (8)-(10) wherein one of the above multiple positions is the 3' position of an anthocyanin.

(12) The present invention also provides a method of acylating a pigment of interest by expressing a single enzyme that has activities of transferring aromatic acyl groups to sugars at multiple positions of an anthocyanin or a gene encoding the enzyme in plants.

(13) The present invention also provides a method of stabilizing a pigment of interest by introducing a single enzyme that has activities of transferring aromatic acyl groups to sugars at multiple positions of an anthocyanin or a gene encoding the enzyme, and acylating the pigment of interest in plants.

(14) The present invention also provides a method of blueing a pigment of interest by introducing a single enzyme that has activities of transferring aromatic acyl groups to sugars at multiple positions of anthocyanin or a gene encoding the enzyme, and acylating the pigment of interest in plants.

(15) The present invention further provides a method according to any of the above (12)-(14) wherein one of the above multiple positions is a sugar at the 3' position of an anthocyanin.

(16) The present invention also provides a plant obtained by an method described in any of the above (12)-(15), a vegetative propagation product or a seed of a plant, or a progeny plant of a plant, a vegetative propagation product or a seed of a plant having properties identical to those of the plant.

(17) The present invention provides a gene encoding a protein having an amino acid sequence as set forth in SEQ ID NO: 4 or 6 and having an activity of transferring an aromatic acyl group to a sugar at the 3' position of anthocyanin, or a gene encoding a protein having a sequence identity of 70% or greater to an amino acid sequence and having an activity of transferring an aromatic acyl group to a sugar at the 3' position of anthocyanin, or a gene encoding a protein having a sequence identity of 70% or greater to the nucleotide sequence as set forth in SEQ ID NO: 3 or 5 and having an activity of transferring an aromatic acyl group to a sugar at the 3' position of anthocyanin.

(18) The present invention provides a gene encoding a protein having an amino acid sequence as set forth in SEQ ID NO: 4 or 6 and having an activity of transferring aromatic acyl groups to sugars at multiple positions of an anthocyanin, or a gene encoding a protein having a sequence identity of 70% or greater to an amino acid sequence and having an activity of transferring aromatic acyl groups to sugars at multiple positions of an anthocyanin, or a gene encoding a protein having a sequence identity of 70% or greater to the nucleotide sequence as set forth in SEQ ID NO: 3 or 5 and having an activity of transferring aromatic acyl groups to sugars at multiple positions of an anthocyanin.

(19) The present invention also provides the gene according to the above (18) wherein one of the multiple positions is a sugar at the 3' position of an anthocyanin.

(20) The present invention also provides a vector comprising the gene according to any of the above (17)-(19).

(21) The present invention also provides a host transformed with the vector according to the above (20).

(22) The present invention also provides a protein encoded by the gene according to any of the above (17)-(19).

(23) The present invention also provides a method of producing a protein having an activity of transferring a sugar to the 3' position of a flavonoid, which method comprises culturing or growing the host according to the above (21), and harvesting the protein from the host.

(24) The present invention also provides a plant in which the gene according to any of the above (17)-(19) has been introduced, or a progeny having properties identical thereto, or a tissue thereof.

(25) The present invention also provides a cut flower of the plant according to the above (24) or a cut flower of a progeny having properties identical thereto.

(26) The present invention also provides a method of acylating the 3' position of anthocyanin, which method comprises using the gene according to any of the above (17)-(19).

(27) The present invention also provides a method of stabilizing anthocyanin, which method comprises using the gene according to any of the above (17)-(19).

(28) The present invention also provides a method of blueing anthocyanin, which method comprises using the gene according to any of the above (17)-(19).

(29) The present invention further provides a method of expressing the gene according to any of the above (17)-(19) in a plant and acylating the pigment of interest in the plant.

(30) The present invention also provides a method of stabilizing a pigment of interest which comprises introducing the gene according to any of the above (17)-(19) to a plant and acylating the pigment of interest in the plant.

(31) The present invention also provides a method of blueing a pigment of interest which comprises introducing the gene according to any of the above (17)-(19) to a plant and acylating the pigment of interest in the plant.

(32) The present invention further provides a method of adding aromatic acyl groups to sugars at multiple positions of an anthocyanin, which comprises using the gene according to any of the above (17)-(19).

(33) The present invention further provides the method according to the above 32 wherein one of the multiple positions is the 3' position of anthocyanin.

BRIEF EXPLANATION OF THE DRAWINGS

FIG. 2 shows the structural formulas, names and abbreviations of anthocyanin compounds related to the present invention.

FIG. 3A is a graph showing time course changes of reaction products when 50 µM of DEL 3G-5G-3'G was used as the substrate. In FIG. 3B, triG represents DEL 3G-5G-3'G, 5Caf represents DEL 3G-5CafG-3'G, 3'Caf represents DEL 3G-5G-3'CafG, and 5,3'Caf represents gentiodelphin (DEL 3G-5CafG-3'CafG).

FIG. 4A is a graph showing time course changes of reaction products when 100 µM of DEL 3G-5G-3'G was used as the substrate. In FIG. 4B, triG represents DEL 3G-5G-3'G, 5Caf represents DEL 3G-5CafG-3'G, 3'Caf represents DEL 3G-5G-3'CafG, and 5,3'Caf represents Gentiodelphin (DEL 3G-5CafG-3'CafG).

In FIG. 5B, triG represents DEL 3G-5G-3'G, 5Caf represents DEL 3G-5CafG-3'G, 3'Caf represents DEL 3G-5G-3'CafG, and 5,3'Caf represents Gentiodelphin (DEL 3G-5CafG-3'CafG).

FIG. 6 shows the result of SDS-PAGE and Western blot of a protein partially purified from the petal of *Gentiana triflora*. The left figure shows the result of SDS-PAGE and the right figure shows the result of Western blot against the GAT4 antibody. In the figure, M represents a molecular marker, lane 1 represents the result of 40-70% ammonium sulfate-saturated precipitate, and lane 2 represents the result of the active fraction after the Dyematrix column.

FIG. 7 shows a result of flower color simulation using the Medio squeeze liquid.

BEST MODE FOR CARRYING OUT THE INVENTION

Figure 1:
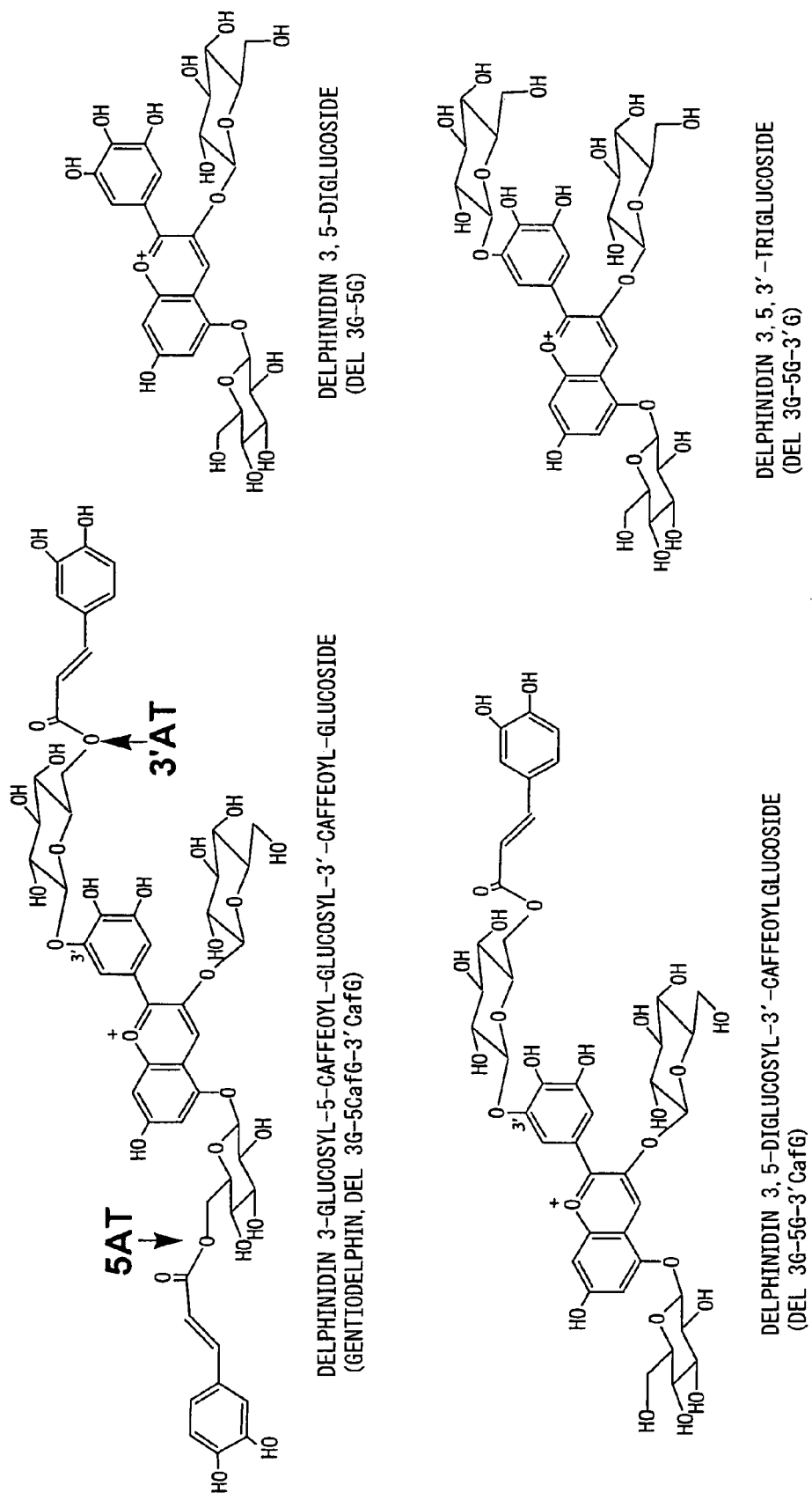
FIG. 1 shows the structural formulas, names and abbreviations of anthocyanin compounds related to the present invention.

Though the present invention describes a method that employs an aromatic acyltransferase that transfers an aromatic acyl group to the 3'-position of anthocyanin or a gene encoding enzyme, genes used and proteins encoded by the gene are not limited to them. Proteins having an amino acid sequence that has been modified by the addition or deletion of a plurality of amino acids, or by replacement with other amino acids are known to maintain the enzyme activity similar to that of the original protein. Thus, as long as the activity of transferring an aromatic acyl group to a sugar at the 3' position has been maintained, protein having an amino acid sequence that has been modified by the addition or deletion of one or a plurality of amino acids, or by replacement with other amino acids, and a gene encoding the protein are also encompassed by the present invention.

The present invention also encompasses a gene encoding a protein that has an amino acid sequence identity of 70% or greater, preferably 90% or greater to the amino acid sequence of the aromatic acyltransferase that transfers an aromatic acyl group to the 3' position of anthocyanin derived from *Gentiana triflora*, amino acid sequence as set forth in SEQ ID NO: 4 or 6, and that has an activity of transferring an aromatic acyl group to a sugar at the 3' position of anthocyanin.

The present invention also encompasses cases which use a gene hybridizing to a gentian DNA encoding an aromatic acyltransferase for a sugar at the 3' position of anthocyanin under a relatively mild condition of 5×SSC and 50° C., and encoding a protein with an activity of transferring an aromatic acyl group to the 3' position. Furthermore, the present invention also encompasses cases which use a gene hybridizing to a gentian DNA encoding an 3'-aromatic acyltransferase under a stringent condition, and encoding a protein with an activity of transferring an aromatic acyl group to the 3' position.

Although the stringent condition as used herein is, for example, 2×SSC and 65° C., it is not limited to this condition since the hybridization condition varies depending on the length and the base composition of DNA used. Genes selected by such hybridization include naturally occurring ones, for example genes derived from plants containing anthocyanin to which an aromatic acyl group has been added at the 3' position, for example genes derived from Clitoria ternatea, lobelia or cineraria, but not limited to those derived from plants. Thus, any genes that encode enzymes having an activity of transferring an aromatic acyl group to the 3' position of anthocyanin may be used. The gene selected by hybridization may be cDNA or genomic DNA.

It is also possible to purify aromatic acyltransferases that transfer aromatic acyl groups to the 3' position from plants such as lobelia and Clitoria ternatea that contain anthocyanin to which an aromatic acyl group has been added to the 3' position by the purification method per se of the enzyme from the *Gentiana triflora* or modifying the method. Furthermore, by determining the amino acid sequence of the purified enzyme, a gene encoding said enzyme can be cloned.

DNA encoding a protein having the altered amino acid sequence can be synthesized using a known site-directed mutagenesis or a PCR method. For example, a DNA fragment of which an amino acid sequence is desired to be altered may be obtained by obtaining cDNA or genomic DNA by restriction enzyme treatment, and, with this as a template, using primers corresponding to the alteration of the desired amino acid sequence, and performing site-directed mutagenesis or a PCR method to obtain a DNA fragment corresponding to the alteration of the desired amino acid sequence. Then, the alteration-introduced DNA fragment may be ligated to a DNA fragment encoding another portion of the enzyme of interest.

Alternatively, in order to obtain a DNA that encodes an enzyme comprising a shortened amino acid sequence, for example, an amino acid sequence longer than the amino acid sequence of interest, for example a full-length amino acid sequence, may be cleaved with the desired restriction enzyme, and if the resulting DNA fragment does not encode the entire amino acid sequence of interest, a DNA fragment corresponding to the amino acid sequence of the lacking part may be synthesized and ligated. By expressing the gene thus obtained in the *Escherichia coli* (*E. coli*) or a yeast expression system, and measuring the activity of transferring an aromatic acyl group to the 3' position in said *E. coli* or yeast extract, the gene obtained may be confirmed to encode an aromatic acyltransferase. A DNA encoding the amino acid sequence of interest may also be synthesized.

The present invention also encompasses cases in which aromatic acyltransferase extracted from recombinant vectors, specifically expression vectors, and host cells transformed with said vectors. As host cells, prokaryotes or eukaryotes may be used. As prokaryotes, there can be used conventional known host cells including, for example, bacteria belonging to genus *Escherichia* such as *Escherichia coli*, microorganisms belonging to genus *Bacillus* such as *Bacillus subtilis*, and the like. As eukaryotes, there can be used, for example, eukaryotic microorganisms, preferably yeast or filamentous fungi.

As the yeast, there can be mentioned yeast of the genus *Saccharomyces* such as *Saccharomyces cereviceae*, and as the filamentous fungi, there can be mentioned microorganisms of the genus *Aspergillus* such as *Aspergillus oryzae* and *Aspergillus niger*, and of the genus *Penicillium*. Furthermore, animal cells or plant cells may be used, and as the animal cells, cell systems such as mice, hamsters, and human cells may be used. Furthermore, insect cells such as silkworm cells or silkworm larvae per se may be used as the host.

Expression vectors may contain expression control regions such as promoters and terminators and replication origins depending on the species of the host into which they are to be introduced. As the promoters of expression vectors for bacteria such as *E. coli*, there can be used conventionally known promoters such as a trc promoter, tac promoter, and lac promoter. As the promoters for yeast, there can be used, for example, the glycerylaldehyde-3-phosphate dehydrogenase promoter and the PH05 promoter, and the promoters for the filamentous fungi include, but not limited to, promoters such as amylase and trpC. Also as the promoters for animal cells, there can be used viral promoters such as the SV40 early promoter and the SV40 late promoter.

Expression vectors may be prepared using restriction enzymes, ligases and the like according to standard methods. Transformation of host cells with expression vectors may also be conducted according to conventionally known methods. As the expression vectors for plants, there can be used binary vectors such as pBI121 when *Agrobacterium* is used, and *E. coli* vectors such as pUC19 when particle guns are used. Furthermore, plant cells that were transformed with said expression vector may be selected with a marker gene such as an antibiotics-resistant gene, and redifferentiated using a condition of a suitable plant hormone, etc. to obtain transformed plants.

The use of aromatic acyltransferase capable of transferring an aromatic acyl group to the 3' position of anthocyanin obtained by culturing or cultivating the thus transformed host cells or transformed plants and recovering and/or purifying from the culture by standard methods such as filtration, centrifugation, cell disruption, gel filtration chromatography and ion exchange chromatography is also encompassed by the present invention.

With the present state of technology in the art, it is possible to introduce a gene into plants and express the gene in a constitutive or tissue-specific manner, and the expression of the gene of interest can also be suppressed by the antisense method or the cosuppression method. Examples of plants that can be transformed include, but not limited to, roses, chrysanthemums, carnations, calceolarias, cyclamens, orchids, prairies gentians, freesias, gerberas, gladioluses, gypsophyllas, kalanchoes, lilies, pelargoniums, geraniums, petunias, torenias, tulips, rice, barley, wheat, rapeseed, potatoes, tomatoes, poplar, bananas, eucalyptus, sweet potatoes, soy beans, alfalfa, lupin, corn, cauliflower and the like.

Thus, those used in the method of aromatic acylation to the 3' position of anthocyanin are not limited to acyltransferases derived from *Gentiana triflora*, or cDNA or gene encoding the enzyme from *Gentiana triflora*, or a recombinant enzyme obtained by expressing the cDNA or gene in a host such as *E. coli*, and aromatic acyltransferases can also be used to transfer aromatic acyl groups to the 3'-position of anthocyanin obtained from a wide variety of other organisms, cDNA or gene encoding the enzymes, or recombinant enzymes obtained by expressing the cDNA or gene in a host such as *E. coli*.

Furthermore, though the present invention used CoA esters such as p-coumaroyl CoA and caffeoyl-CoA as the donor for the acyl group, p-coumaroyl or hydroxy cinnamoyl-1-O-glucose such as cinnapoyl-1-O-glucose may also be used as the donor for the acyl group (Glassgen and Seitz, Planta 186: 582, 1992), and thus these may be used as the enzyme claimed in the present invention.

EXAMPLES

The present invention will now be explained in more detail with reference to specific embodiments. Unless otherwise specified, experimental procedures were as described in Sambrook et al., Molecular Cloning (Cold Spring Harbor Laboratory Press, 1989), PCT-JP96-00348, and reports by Fujisawa et al. (1997, 1998).

Example 1

Expression of cDNA of *Gentiana triflora*-Derive Acyl Transferase in *Escherichia coli* and Purification of Recombinant Protein By cleaving a construct pGeAT102 (Fujiwara et al., Plant J., 16, 421, 1998) for *E. coli* expression of cDNA of *Gentiana triflora*-derived acyltransferase with NcoI/HindIII, a fragment containing the coding region of the acyltransferase and the 3'-untranslated region was subcloned to the NcoI/HindIII site of *E. coli* expression vector pQE60 (QIAGEN) to obtain a construct pQE8 for *E. coli* expression.

An *E. coli* strain JM109, in which pQE8 was introduced was cultured in a SB medium at 37° C. to OD600 nm=0.8, and then further cultured at a reduced temperature of 15° C. for 1 hour, to which IPTG was added to a final concentration of 0.1M to induce the expression of the gene of *Gentiana triflora* acyltransferase. After culturing at 15° C. for 1 hour, cells were collected and sonication-disrupted, and used in the following purification. The disrupted cells were subjected to DE52 (Whatman), and the flow-through fraction with 25 mM Tris-HCl (pH 7.5) containing 150 mM NaCl was collected. Salting out with ammonium sulfate was further performed to collect a 40-60% ammonium sulfate-saturated fraction, which was dissolved in a small amount of 20 mM Tris-HCl (pH 7.5) and dialized using Sephadex G-25 (Pharmacia) equilibrated with 20 mM Tris-HCl (pH 7.5).

After this was loaded to DEAE-TOYOPEARL (TOSOH Corporation), and eluted with a linear gradient of 0 to 0.5 M NaCl-containing in 20 mM Tris-HCl (pH 7.5), an activity of 5-acyltransferase to delphinidin 3,5-diglucoside (DEL 3G-5G) was present in the eluted fraction of 120-240 mM NaCl. The active fraction was dialyzed against a 20 mM Tris-HCl (pH 7.5), and then loaded to Blue Sepharose (Pharmacia). No activity was found in the flow-through fraction of Blue Sepharose, and the adsorbed fraction was eluted with 20 mM Tris-HCl (pH 7.5) containing 1 M NaCl.

Subsequently, this fraction was adsorbed to Phenyl Sepharose (Pharmacia), and eluted with a linear gradient of 40 to 0% ammonium sulfate in 20 mM Tris-HCl (pH 7.5). The active fraction was eluted with 0% ammonium sulfate. This was dialyzed against 20 mM Tris-HCl (pH 7.5), then allowed to adsorb to Dyematrix column Orange A (Amicon), and eluted with 10 mM Tris-HCl (pH 7.5) containing 0.3 M NaCl and 0.5 mM DTT. No activity was found in the flow-through fraction, and the activity was only found in the adsorbed fraction, which was concentrated with Centricon-10 (Amicon).

Example 2

Measurement of Activity of Recombinant Acyltransferase

The enzymatic activity of the recombinant enzyme obtained in Example 1 was measured with 3 types of delphinidin derivatives (delphinidin 3,5,3'-triglucoside (DEL 3G-5G-3'G), delphinidin 3-glucosyl-5-caffeoylglucosyl-3'-glucoside (DEL 3G-5CafG-3'G), delphinidin 3-glucosyl-5-glucosyl-3'-caffeoylglucoside (DEL 3G-5G-3'CafG)) shown in FIG. 1 and FIG. 2 as substrates. The reaction mixture contained 100 mM potassium phosphate buffer (pH 8.5), 0.2 mM caffeoyl-CoA, 250 mM each of the above substrates and 5 μl of the enzyme solution in a total volume of 50 μl, and the reaction was carried out at 30° C. for 15 minutes. An equal volume of 90% acetonitrile solution containing 0.1% trifluoroacetic acid (TFA) was added to the reaction mixture to stop the reaction.

In order to analyze time course changes of reaction products, 5 μl of a 25-fold diluted enzyme solution and each of 50 μM, 100 μM or 200 μM of DEL 3G-5G-3'G were used as a substrate, and the reaction was stopped at 2.5, 5, 10, and 20 minutes later to analyze the products. The reaction products were analyzed with a reverse phase high performance liquid chromatography (HPLC) using a DE-41 column (4.6×250 mm, Shodex). Samples were eluted with an liner gradient of 20-50% of acetonitrile containing 0.5% TFA at 0.6 ml/min for 15 minutes, and then isoclatic elution at 0.6 ml/min for 10 minutes, and detected with SPD-M10A (SHIMAZU Corporation) at a wavelength of 250-600 nm. The HPLC elution time and absorption spectra of products were compared with those of authentic samples to identify the structure of products.

As a result of reaction using the above three types of compounds as the substrate, the recombinant acyltransferase reacted with all of the substrates. With 250 mM DEL 3G-5CafG-3'G as the substrate, 94.1% was converted to DEL 3G-5CafG-3'CafG. On the other hand, with 250 mM DEL 3G-5G-3'CafG as the substrate, 95.2% was converted to DEL 3G-5CafG-3'CafG. When 250 mM DEL 3G-5G-3'G was used as a substrate, 7.2% was converted to DEL 3G-5CafG-3'G to which an aromatic acyl group was added at the 5 position alone, and 58.7% was converted to DEL 3G-5CafG-3'CafG, while only the trace amount of DEL 3G-5G-3'CafG was produced, to which an aromatic acyl group was added at the 3' position alone (1% or less).

Figure 3:
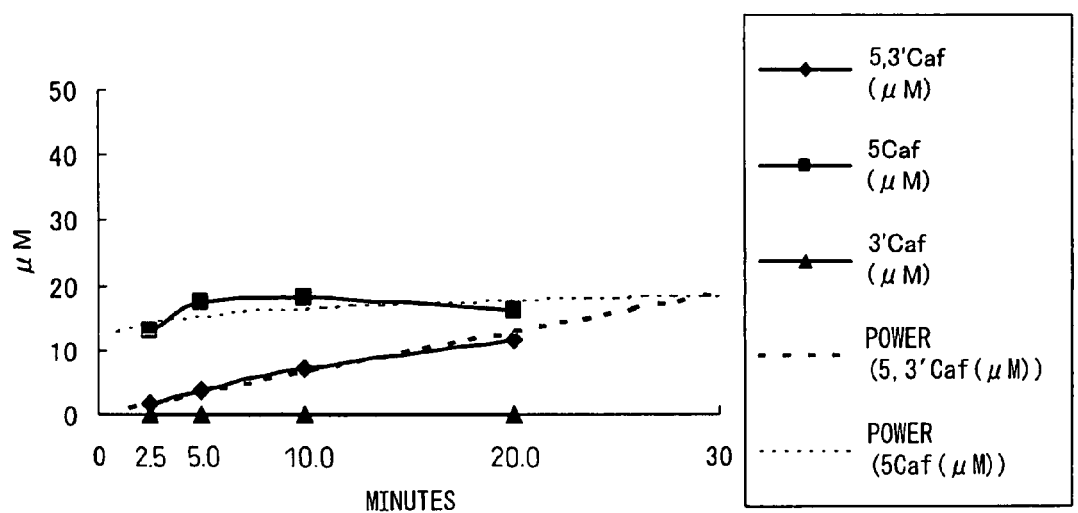
FIGS. 3A-3B.
Figure 4:
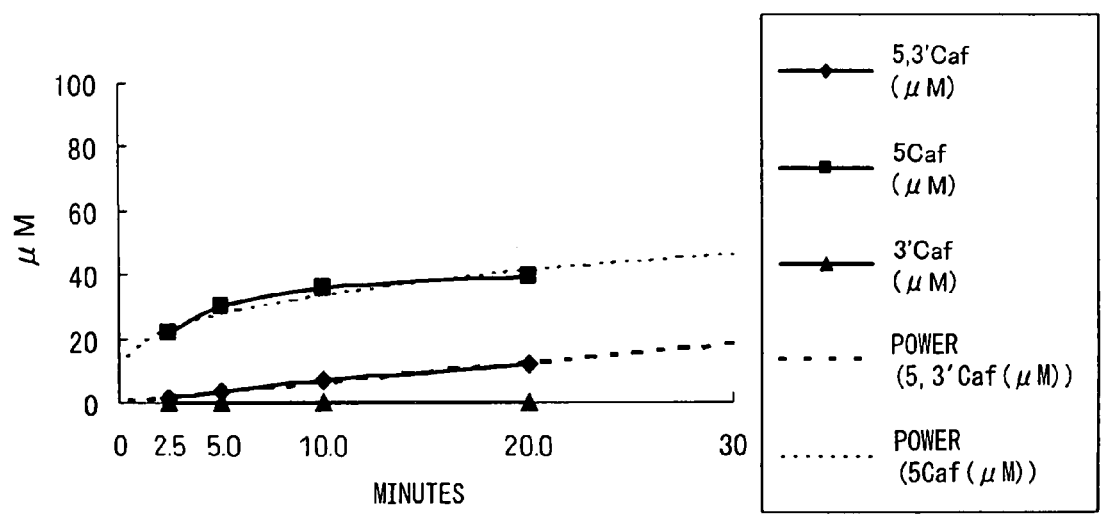
FIGS. 4A-4B.
Figure 5:
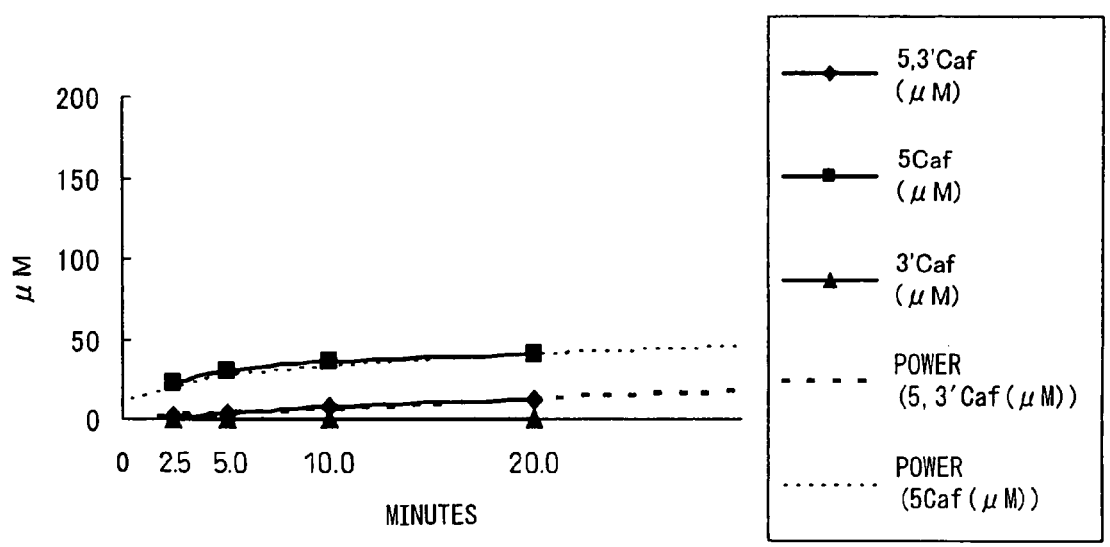
FIGS. 5A-5B is a graph showing time course changes of reaction products when 200 µM of DEL 3G-5G-3'G was used as the substrate.

When the time course changes of the reaction was measured using a diluted enzyme solution with DEL 3G-5G-3'G as a substrate, the amount produced of DEL 3G-5CafG-3'G and DEL 3G-5CafG-3'CafG increased according to the reaction time. The amount of DEL 3G-5G-3'CafG was much smaller than the other two substrates, and barely detected when the amount of the substrate and the reaction time were increased (FIG. 3, FIG. 4, and FIG. 5). This result consistent with those obtained when the undiluted enzyme solution was reacted to DEL 3G-5G-3'G.

From the above result, it was revealed that a recombinant protein obtained by expressing the gene of an acyltransferase derived from *Gentiana triflora* in *E. coli* has an activity of transferring acyl groups to sugars on both the 5 position and the 3' position of anthocyanin. Thus, although a previous report (Fujiwara et al., Plant J., 16, 421, 1998) showed that this enzyme was thought to transfer an aromatic acyl group only to the 5 position of anthocyanin, the present invention revealed that this enzyme transfers aromatic acyl groups to sugars at both of the 5 and the 3' position of anthocyanin. Furthermore, considering the reaction products with DEL 3G-5G-3'G as a substrate, it is likely that the addition of an aromatic acyl group to the 5-glucose precedes the addition to the 3'-glucose.

Example 3

Purification of Aromatic Acyl Group Transferase Derived from *Gentiana triflora*

The recombinant protein obtained by expressing a gentian cDNA of an aromatic acyltransferase in *E. coli* turned out to have an activity of transferring aromatic acyl groups to glucoses at the 5 and the 3' position of a anthocyanin (Example 2). In order to confirm that an enzyme naturally occurring in gentian petals also has both activities of the 5-aromatic acyltransferase and the 3'-aromatic acyl transferase, this enzyme was purified from gentian petals. In a series of purification, as described in Example 2, each eluted fraction of column chromatography was measured for 5-aromatic acyltransferase activity with DEL 3G-5G as a substrate and for 3'-aromatic acyltransferase activity with DEL 3G-5G-3'G as a substrate.

According to a report by Fujiwara et al. (Fujiwara et al., Eur. J. Biochem. 249: 45, 1997) in which a gentian 5-aromatic acyltransferase was purified, 40-70% ammonium sulfate-saturated fraction was obtained from extract of approximately 100 g of *Gentiana* petals. This fraction was dialyzed with Sephadex G-25 (Pharmacia) equilibrated with 20 mM Tris-HCl (pH 7.0) containing 10 μM p-aminophenylmethanesulfonyl fluoride (APMSF) and 1 mM DTT (hereinafter referred to as the Tris buffer), then it was loaded to MONO Q (Pharmacia) equilibrated with the Tris buffer. The unadsorbed fraction was washed off with the Tris buffer, and then eluted with a liner gradient of 0-0.5 M NaCl in the Tris buffer at a flow rate of 5 ml/min for 20 minutes. The activity of transferring an aromatic acyl group was present in fractions eluted at 0.2-0.42 M NaCl.

The active fractions were loaded to HiTrap Blue (Pharmacia) and extensively washed in the Tris buffer, and then the adsorbed fraction was eluted with a Tris buffer containing 0.9 M NaCl. The activity was present in the adsorbed fraction. Then, the active fraction was loaded to a DEAE-Sepharose (Pharmacia). After extensively washing with the Tris buffer, the adsorbed fraction was eluted with a linear gradient os 0-0.5M NaCl in the Tris buffer at 0.5 ml/min for 60 minutes. The activity was found in the fractions eluted with 0.22-0.3 mM NaCl. The active fraction concentrated with Centricon 30 (Amicon) was loaded to a Dyematrix column Red (Amicon). After washing off the unabsorbed fraction with the Tris buffer, the adsorbed fraction was eluted with the Tris buffer containing 1.5 M KCl. When the eluted protein was subject to SDS-PAGE, only a single band was detected at molecular weight of 52 kDa which is an estimated molecular weight for an anthocyanin 5-acyltransferase.

In a series of purifications, each eluted fraction of column chromatography was measured for the 5-aromatic acyltransferase activity with DEL 3G-5G as a substrate and for the 5,3'-aromatic acyltransferase activity with DEL 3G-5G-3'G as a substrate, and the fractions with the highest activity in both acyltransferase reactions were completely identical. When activities for three types of substrates (DEL 3G-5G-3'G, DEL 3G-5CafG-3'G, DEL 3G-5G-3'CafG) were measured using the active fraction that adsorbed to the Dyematrix column Red as in Example 2, all of the substrates reacted and exhibited characteristics similar to those of Example 2.

After the active fraction that absorbed to the Dyematrix column Red was separated with SDS polyacrylamide gel electrophoresis, the separated protein was transferred to a nitrocellulose membrane Hybond-ECL (Amersham) according to the method described before (Towbin et al., Proc. Natl. Acad. Sci. 76: 4350, 1979), and crossed against an antibody specific to a gentian 5-anthocyanin acyltransferase (Fujiwara et al., Eur. J. Biochem. 249: 45, 1997) in a Western blotting, which detected one clear band (FIG. 6).

These results revealed that the anthocyanin 3'-acyltransferase activity and the anthocyanin 5-acyltransferase activity present in gentian petals were derived from a single protein.

Example 4

Stabilization and Bluing of Anthocyanin with an Acyltransferase Derived from *Gentiana triflora*

Relative stability of DEL 3G-5G-3'G, DEL 3G-5CafG-3'G, DEL 3G-5G-3'CafG and DEL 3G-5CafG-3'CafG has already been reported; in an aqueous solution of pH 6.5, DEL 3G-5CafG-3'CafG is most stable and refractory to fading, followed by DEL 3G-5G-3'CafG, DEL 3G-5CafG-3'G, and DEL 3G-5G-3'G in this order (Yoshida et al., Phytochemistry 54: 85, 2000). As for the absorbance maximum, that for DEL 3G-5CafG-3'CafG is the longest wavelength followed by DEL 3G-5G-3'CafG, DEL 3G-5CafG-3'G and DEL 3G-5G-3'G in this order. Thus, this report shows that DEL 3G-5CafG-3'CafG exhibit the most blueish in surface followed by DEL 3G-5G-3'CafG (Yoshida et al., Phytochemistry 54: 85, 2000).

In order to simulate the flower color when the gene for gentian anthocyanin 5,3'-acyltransferase was introduced into roses and DEL 3G-5CafG-3'CafG was accumulated in rose petals, the color development of a purified pigment suspended in juice squeezed form rose petals (cv. Medeo) was measured. As for purified pigments, DEL 3G-5CafG-3'CafG, and as a comparative control, DEL 3G-5G, cyanidin 3,5-diglucoside (CYA 3G-5G), pelargonidin 3,5-diglucoside (PEL 3G-5G) and malvidin 3,5-diglucoside (MAL 3G-5G) were used. About 20 g of Medeo petals frozen at −80° C. for more than one hour were squeezed by a garlic squeezer for household use, and centrifuged at 1000 rpm for 1 minute to remove the debris of the petals, and the supernatant was prepared as the squeezed juice.

Twenty μl of 50 mM DMSO solution of purified pigment was added to 1 ml of the squeezed juice, and kept for 10 minutes, and the absorption and transmittance spectra at 380-780 nm were measured with a spectrophotometer UV-2500PC(SHIMADZU Corporation). The transmittance spectrum values were converted into CIE L*a*b* color system (JISZ8729). The Royal Horticultural Society color chart (RHSCC) number was referenced based on the color value (CIE L*a*b* color system) to check the approximate colors using the color classification system Version 2.1.1 (The Japan Research Institute, Co. Ltd., Japan; Japanese Unexamined Patent Publication No. 2002-016935). By using this system, an approximate RHSCC number can be objectively selected. The final concentration of the pigment added to the squeezed juice approximately identical to the average anthocyanin concentration in the vacuoles of rose petals. However, since the absorbance for 3G-5CafG-3'CafG was too high, it was diluted 4-fold prior to measurement. Medeo is a variety that shows an average petal pH (pH 4.38) among the garden species of roses.

As shown in FIG. 7, DEL 3G-5CafG-3'CafG exhibited the largest maximum absorption spectrum among five purified pigments. The approximate color was 89A in the Royal Horticultural Society color chart (RHSCC), which was obtained based on the L*a*b* value converted from the transmission spectrum, and the DEL 3G-5CafG-3'CafG exhibited the strongest blue color among the five purified pigments as shown in FIG. 7.

From this result, it seems to be possible to produce DEL 3G-5CafG-3'CafG in rose petals and as a result to produce rose flowers with blue color by coexpressing the genes for anthocyanin 5,3'-aromatic acyltransferase, the F3'5'H gene (WO 2004/020637) and the gene of 3'-glycosyltransferase (WO 2001/92509) in rose petals. Also it seems to be possible to create blue flower varieties in carnations, chrysanthemums, petunias, verbenas, *nierembergias*, lilies and so on.

Example 5

Isolation of 5,3'-Position Aromatic Acyltransferase Homolog of Anthocyanin from *Gentiana triflora*-Related Species In the genus *Gentiana*, there are various related species such as *Gentiana rubicunda* and *Gentiana yakushimensis* in addition to *Gentiana triflora*. Isolation of 5,3'-aromatic acyltransferase homolog from these species was attempted by PCR.

Since the gene for gentian 5,3'-aromatic acyltransferase was known to contain no introns, genomic DNAs extracted from the leaves of the related species were used as templates in PCR with primers specific for the gene of 5,3'-aromatic acyltransferase. An QIAGEN's DNeasy kit was used for the extraction of genomic DNA following a method recommended by the manufacturer. Primers, GAT4-Met-F and GAT4-B, specific for the gene of 5,3'-acyltransferase had the following sequences, and the full-length cDNA containing the entire coding region can be amplified by PCR using these primers. The reaction condition for PCR is as described below.

Sequences of Primers:

```
GAT4-Met-F:
TCA TTA TGG AGC AAA TCC AAA        (SEQ ID NO: 1)

GAT4-B:
CAT GTC AGG TGT GAG GTT CAA C      (SEQ ID NO: 2)
```

PCR condition:
Denaturation reaction: 94° C. for 5 minutes, 1 cycle
Amplification reaction: 94° C. for 1 minute, 55° C. for 1 minute 30 seconds, 72° C. for 3 minutes, 30 cycles
Extension reaction: 72° C. for 7 minutes, 1 cycle In this PCR, a band at expected size, 1.5 kb, was amplified in three related species, *Gentiana yakushimensis, ochroleuca* and *wutaiensis*. These fragments were collected and cloned into a pCRII-TOPO (Invitrogen) and their nucleotide sequences were determined. The nucleotide sequences and the corresponding amino acid sequences of the amplified fragments obtained from each species are shown in Sequence Listing.

*Gentiana yakushimensis*: SEQ ID NO: 3 and 4
*Gentiana ochroleuca* and *wutaiensis*: SEQ ID NO: 5 and 6

Fragments obtained from *ochroleuca* and *wutaiensis* turned out to encode the identical amino acid sequence. The identity with 5,3'-aromatic acyltransferase first obtained from *Gentiana triflora* was 95% for that from *Gentiana yakushimensis* and 90% for those obtained from *ochroleuca* and *wutaiensis*. From this high identity, the proteins encoded in these DNAs seem to be homologs to 5,3'-aromatic acyltransferase.

Example 6

Expression of 5,3'-Aromatic Acyltransferase of Anthocyanin from *Gentiana triflora* in *nierembergia*

The gene for 5,3'-aromatic acyltransferase from *Gentiana triflora* was introduced into *nierembergia* together with the genes for gentian 3'-glucosyltransferase and for pansy F3'5'H gene. In transformants, it is expected that the 3' position of DEL 3G-5G was first glucosylated by gentian 3'-glucosyltransferase to form DEL 3G-5G-3'G, on which gentian 5,3'-aromatic acyltransferase may act to form a final product gentiodelphin (DEL 3G-5CafG-3'CafG).

A expression construct pSPB1536 was prepared by introducing an expression cassette of 3'-glucosyltransferase into the HindIII and the EcoRI sites of a binary vector for expression in plants (van Engelen F A et al. (1995) Transgenic Res. 4: 288-290), an expression cassette of pansy F3'5'H into the PadI site and an expression cassette of 5,3'-aromatic acyltransferase into the AscI site. Any of the expression cassettes is regulated by the 35S promoter derived from a cauliflower mosaic virus, and has the *Agrobacterium*-derived nopaline synthase terminator sequence downstream to each structural gene. Transformation of *nierembergia* was conducted as described in a report by Tanaka et al. (Tanaka et al. (2005) Plant Cell Tiss. Org. Cult. 80: 1-24).

The expression of three genes (gentian 5,3'-aromatic acyltransferase gene, gentian 3'-glycosyl transferase gene, and pansy F3'5'H gene) in *nierembergia* transformants was confirmed by RT-PCR. For the lines where transcription of all three genes were confirmed, the petal color was analyzed in a similar manner to that described in a report by Mizutani et al. (Fukuchi-Mizutani et al. (2003) Plant Physiol. 132: 1652-1663), but the expected final product gentiodelphin was not detected in any of the lines.

On the other hand, a crude enzyme was extracted from the petals of the transformants where transcription of all three genes were confirmed, in a manner as described in the report by Fujiwara et al. (Fujiwara et al., (1997) Eur. J. Biochem. 249: 45-51). Using this crude extract as a enzyme solution, in vitro activity of 5,3'-aromatic acyltransferase was measured with DEL 3G-5G-3'G as the substrate in a manner similar to Example 2, then, formation of gentiodelphin was confirmed. On the other hand, when the crude enzyme from a non-recombinant *nierembergia* was used as the control, gentiodelphin was not detected. This result revealed that the transgenic *nierembergia* has 5,3'-aromatic acyltransferase activity, i.e., an activity of transferring aromatic acyl groups to both 5 and 3' position of DEL 3G-5G-3'G used as a substrate.

However, when the activity of the 3'-glucosyltransferase was measured in vitro as described in a report by Mizutani et al. (Fukuchi-Mizutani et al. (2003) Plant Physiol. 132: 1652-1663) with crude enzyme solution from *nierembergia* transformants, no 3'-glucosyltransferase activity was detected. These results confirmed that a protein with an activity of 5,3'-aromatic acyltransferase is indeed present in the cell of the *nierembergia* transformants. However, the reason why the expected gentiodelphin was not detected in the petals of the transformants was because the protein of the 3'-glucosyltransferase that should work prior to the 5,3'-aromatic acyltransferase was not synthesized in the cell of *nierembergia*, or did not function even if it was synthesized.

EFFECT OF THE INVENTION

As described above, the present invention has demonstrated that a recombinant aromatic acyltransferase obtained by expressing a gentian aromatic acyltransferase gene in *E. coli* has an activity of transferring aromatic acyl groups not only to a sugar at the 5 position of delphinidin glucosides, but also to a sugar at the 3' position thereof. It further revealed that the naturally occurring anthocyanin 5-aromatic acyltransferase purified from gentian petals also has an activity of transferring an aromatic acyl group to a sugar at the 3' position, i.e., unlike the conventional anthocyanin aromatic acyltransferase, a single enzyme transfers aromatic acyl groups to sugars at both 5 position and 3' position of an anthocyanin.

Furthermore, it was possible to express this gene in different species of plants, thus to obtain the 5,3'-aromatic acyltransferase activity.

It is generally believed that the aromatic acyl group at the 3' position contributes to the stabilization and blueing of anthocyanin more strongly than the aromatic acyl group at the 5 position, and the presence of sugar-acyl side chains at multiple positions including 3' position is more preferred. Thus, as described in the present invention, it is possible to create an anthocyanin that has a more stable and bluish hue by conducting aromatic acylation at both 5 and 3' position of an anthocyanin glucosides using a 5,3'-aromatic acyltransferase that transfers aromatic acyl groups to both 5 and 3' position. Furthermore, by expressing the gene for the said enzyme in plants together with other genes essential for anthocyanin biosynthesis or anthocyanin modification, it is possible to make flower color, mainly comprising of anthocyanins, more stable and bluer.

The invention claimed is:

1. An isolated gene encoding a protein having the amino acid sequence of SEQ ID NO: 4 or 6 and having an activity of transferring aromatic acyl groups to sugars at the 3' and 5 positions of an anthocyanin, or an isolated gene encoding a protein having a sequence identity of 93% or greater to the amino acid sequence of SEQ ID NO: 6 and having an activity of transferring aromatic acyl groups to sugars at the 3' and 5 positions of an anthocyanin.

2. A vector comprising the gene according to claim 1.

3. A host comprising the vector according to claim 2, wherein said host is a bacterial cell, fungal cell, yeast cell, plant cell or plant.

4. An isolated protein encoded by the gene according to claim 1.

5. A method of producing the protein encoded by the gene according to claim 1, comprising culturing or growing a host comprising a vector which comprises the gene according to claim 1, and harvesting said protein from the host; wherein said host is a bacterial cell, fungal cell, yeast cell, plant cell or plant.

6. A plant comprising the gene according to claim 1, or a progeny comprising said gene, or a tissue thereof.

7. A cut flower of the plant or progeny according to claim 6.

8. A method of acylating the 3' and 5 positions of an anthocyanin, which method comprises expressing the gene according to claim 1 in a plant, wherein said plant comprises a vector which comprises the gene.

* * * * *

```
                        SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tcattatgga gcaaatccaa a                                              21

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
catgtcaggt gtgaggttca ac                                             22

<210> SEQ ID NO 3
<211> LENGTH: 1603
<212> TYPE: DNA
<213> ORGANISM: Gentiana yakushimensis
<220> FEATURE:
<221> NAME/KEY: CDS
<222> LOCATION: (6)..(1412)

<400> SEQUENCE: 3 tcatt atg gag caa atc caa atg gcg aag gtt gtt gaa aaa tgc caa gtt      50
      Met Glu Gln Ile Gln Met Ala Lys Val Val Glu Lys Cys Gln Val
      1               5                   10                  15 aca cca cca ttt gac aca aca gat gtc gag tta tca gta ccg gta aca      98
Thr Pro Pro Phe Asp Thr Thr Asp Val Glu Leu Ser Val Pro Val Thr
             20                  25                  30 ttc ttt gat atc ccc tgg ttg cac ttg tat aag atg cag tcc ctt ctg     146
Phe Phe Asp Ile Pro Trp Leu His Leu Tyr Lys Met Gln Ser Leu Leu
         35                  40                  45 ttt tac gac ttt ccg tac cca aaa aca cat ttc ttg gac act gtt atc     194
Phe Tyr Asp Phe Pro Tyr Pro Lys Thr His Phe Leu Asp Thr Val Ile
     50                  55                  60 cct aat ctt aag gcc tct ttg tct ctc act cta aaa cac tac ctt ccg     242
Pro Asn Leu Lys Ala Ser Leu Ser Leu Thr Leu Lys His Tyr Leu Pro
 65                  70                  75 ctt agt gga aat ttg tta atg ccc atc aaa tcg ggc aaa atg cca aag     290
Leu Ser Gly Asn Leu Leu Met Pro Ile Lys Ser Gly Lys Met Pro Lys
 80                  85                  90                  95 ttt cac tac tcc cgt gat gac gga gac tcg ata act ttg atc ttt gcg     338
Phe His Tyr Ser Arg Asp Asp Gly Asp Ser Ile Thr Leu Ile Phe Ala
                100                 105                 110
```

-continued

| | | |
|---|---|---|
| gag tct gac cag gat ttt gac tac ctt aaa ggt cat caa ctg gta gat<br>Glu Ser Asp Gln Asp Phe Asp Tyr Leu Lys Gly His Gln Leu Val Asp<br>115                     120                   125 | | 386 |
| tcc aat gat ttg cat gcc ctt ttt tat gtt atg cca cgg gtt ata agg<br>Ser Asn Asp Leu His Ala Leu Phe Tyr Val Met Pro Arg Val Ile Arg<br>    130                   135                  140 | | 434 |
| acc atg caa gac tat aaa gtg atc ccg ctc gta gct gtg caa gta acc<br>Thr Met Gln Asp Tyr Lys Val Ile Pro Leu Val Ala Val Gln Val Thr<br>145                     150                   155 | | 482 |
| gtt ttt cct aac cat ggc ata gcc gtg gct ctg acg gca cat cat tca<br>Val Phe Pro Asn His Gly Ile Ala Val Ala Leu Thr Ala His His Ser<br>160                     165                  170                  175 | | 530 |
| att gca gat gct aaa agt ttt gta atg ttc atc aat gct tgg gcc tat<br>Ile Ala Asp Ala Lys Ser Phe Val Met Phe Ile Asn Ala Trp Ala Tyr<br>                  180                  185                  190 | | 578 |
| att aac aaa ttt ggg aaa gac gcg gac ttg ttg tcc gcg aat ctt ctt<br>Ile Asn Lys Phe Gly Lys Asp Ala Asp Leu Leu Ser Ala Asn Leu Leu<br>                 195                  200                  205 | | 626 |
| cca tct ttt gat aga tcg ata atc aaa gat ctg tat ggc cta gag gaa<br>Pro Ser Phe Asp Arg Ser Ile Ile Lys Asp Leu Tyr Gly Leu Glu Glu<br>210                     215                   220 | | 674 |
| aca ttt tgg aac gaa atg caa gat att ctt gaa atg ttc tct aca ttt<br>Thr Phe Trp Asn Glu Met Gln Asp Ile Leu Glu Met Phe Ser Thr Phe<br>    225                   230                  235 | | 722 |
| gga agc aaa ccc cct cga ttc aac aag gta cga gct gca tat gtc cta<br>Gly Ser Lys Pro Pro Arg Phe Asn Lys Val Arg Ala Ala Tyr Val Leu<br>240                     245                  250                  255 | | 770 |
| tcc ctt gct gaa atc cag aag cta aag aac aaa gta ctg aat ctc aga<br>Ser Leu Ala Glu Ile Gln Lys Leu Lys Asn Lys Val Leu Asn Leu Arg<br>                  260                  265                  270 | | 818 |
| gga tcc gaa ccg aca ata cgt gta acg acg ttc aca gtg aca tgt gga<br>Gly Ser Glu Pro Thr Ile Arg Val Thr Thr Phe Thr Val Thr Cys Gly<br>                 275                  280                  285 | | 866 |
| tac gta tgg aca tgc atg gtc aaa tca aaa gat gac gtt gta tca gag<br>Tyr Val Trp Thr Cys Met Val Lys Ser Lys Asp Asp Val Val Ser Glu<br>             290                  295                  300 | | 914 |
| gaa tca tcg aac gac gaa aat gag ctc gag tac ttc agt ttt aca gcg<br>Glu Ser Ser Asn Asp Glu Asn Glu Leu Glu Tyr Phe Ser Phe Thr Ala<br>305                     310                   315 | | 962 |
| gat tgc cga gga ctt ctg acg ccc ccg tgt ccg cct aac tac ttt ggc<br>Asp Cys Arg Gly Leu Leu Thr Pro Pro Cys Pro Pro Asn Tyr Phe Gly<br>320                     325                   330                  335 | | 1010 |
| aac tgt ctt gcg tca tgc gtt gca aaa gca aca cat aaa gag tta gtt<br>Asn Cys Leu Ala Ser Cys Val Ala Lys Ala Thr His Lys Glu Leu Val<br>                  340                  345                  350 | | 1058 |
| ggg aat aaa ggg ctt ctt gtt gca gtt gca gct att gta gaa gcc att<br>Gly Asn Lys Gly Leu Leu Val Ala Val Ala Ala Ile Val Glu Ala Ile<br>                 355                  360                  365 | | 1106 |
| gaa aag agg gtg cac aac gaa aaa ggc gtt ctt gca gat gca aaa act<br>Glu Lys Arg Val His Asn Glu Lys Gly Val Leu Ala Asp Ala Lys Thr<br>             370                  375                  380 | | 1154 |
| tgg tta tcg gaa tct aat gga atc cct tca aaa aga ttt ctc ggc att<br>Trp Leu Ser Glu Ser Asn Gly Ile Pro Ser Lys Arg Phe Leu Gly Ile<br>385                     390                   395 | | 1202 |
| act gga tca cct aag ttt gat tcg tat ggt gta gat ttt gga tgg gga<br>Thr Gly Ser Pro Lys Phe Asp Ser Tyr Gly Val Asp Phe Gly Trp Gly<br>400                     405                   410                  415 | | 1250 |
| aag cct gca aaa ttt gac att acc tct att gat tat gca gaa ttg att<br>Lys Pro Ala Lys Phe Asp Ile Thr Ser Ile Asp Tyr Ala Glu Leu Ile<br>                  420                  425                  430 | | 1298 |

```
tat gtg att gag tcc agg gat ttt gaa aaa ggt gtg gag atc gga gta    1346
Tyr Val Ile Glu Ser Arg Asp Phe Glu Lys Gly Val Glu Ile Gly Val
            435                 440                 445 tca ttg ccc aag att cat atg gat gca ttt gca aaa atc ttt gaa gaa    1394
Ser Leu Pro Lys Ile His Met Asp Ala Phe Ala Lys Ile Phe Glu Glu
        450                 455                 460 ggt ttt tgc ttt ttg tca tagtctcttt aatagaacca tatttgctgc           1442
Gly Phe Cys Phe Leu Ser
    465 aataaagtac gaagtcttta gtaacactac accaaaccct actttcgagg caggaacacc  1502 acaacaacga ggttcaatca ctagaaggtt gtacttcata aattccagag gtcgaatatc  1562 caccgttgtc ctatgaaaag ttgaacctca cacctgacat g                      1603

<210> SEQ ID NO 4
<211> LENGTH: 469
<212> TYPE: PRT
<213> ORGANISM: Gentiana yakushimensis

<400> SEQUENCE: 4

Met Glu Gln Ile Gln Met Ala Lys Val Val Glu Lys Cys Gln Val Thr
  1               5                  10                  15

Pro Pro Phe Asp Thr Thr Asp Val Glu Leu Ser Val Pro Val Thr Phe
             20                  25                  30

Phe Asp Ile Pro Trp Leu His Leu Tyr Lys Met Gln Ser Leu Leu Phe
         35                  40                  45

Tyr Asp Phe Pro Tyr Pro Lys Thr His Phe Leu Asp Thr Val Ile Pro
     50                  55                  60

Asn Leu Lys Ala Ser Leu Ser Leu Thr Leu Lys His Tyr Leu Pro Leu
 65                  70                  75                  80

Ser Gly Asn Leu Leu Met Pro Ile Lys Ser Gly Lys Met Pro Lys Phe
                 85                  90                  95

His Tyr Ser Arg Asp Asp Gly Asp Ser Ile Thr Leu Ile Phe Ala Glu
            100                 105                 110

Ser Asp Gln Asp Phe Asp Tyr Leu Lys Gly His Gln Leu Val Asp Ser
        115                 120                 125

Asn Asp Leu His Ala Leu Phe Tyr Val Met Pro Arg Val Ile Arg Thr
    130                 135                 140

Met Gln Asp Tyr Lys Val Ile Pro Leu Val Ala Val Gln Val Thr Val
145                 150                 155                 160

Phe Pro Asn His Gly Ile Ala Val Ala Leu Thr Ala His His Ser Ile
                165                 170                 175

Ala Asp Ala Lys Ser Phe Val Met Phe Ile Asn Ala Trp Ala Tyr Ile
            180                 185                 190

Asn Lys Phe Gly Lys Asp Ala Asp Leu Leu Ser Ala Asn Leu Leu Pro
        195                 200                 205

Ser Phe Asp Arg Ser Ile Ile Lys Asp Leu Tyr Gly Leu Glu Glu Thr
    210                 215                 220

Phe Trp Asn Glu Met Gln Asp Ile Leu Glu Met Phe Ser Thr Phe Gly
225                 230                 235                 240

Ser Lys Pro Pro Arg Phe Asn Lys Val Arg Ala Ala Tyr Val Leu Ser
                245                 250                 255

Leu Ala Glu Ile Gln Lys Leu Lys Asn Lys Val Leu Asn Leu Arg Gly
            260                 265                 270

Ser Glu Pro Thr Ile Arg Val Thr Thr Phe Thr Val Thr Cys Gly Tyr
        275                 280                 285
```

```
Val Trp Thr Cys Met Val Lys Ser Lys Asp Val Val Ser Glu Glu
    290             295                 300

Ser Ser Asn Asp Glu Asn Glu Leu Glu Tyr Phe Ser Phe Thr Ala Asp
305             310              315                 320

Cys Arg Gly Leu Leu Thr Pro Pro Cys Pro Asn Tyr Phe Gly Asn
                325             330                 335

Cys Leu Ala Ser Cys Val Ala Lys Ala Thr His Lys Glu Leu Val Gly
            340             345                 350

Asn Lys Gly Leu Leu Val Ala Ala Ile Val Glu Ala Ile Glu
        355             360             365

Lys Arg Val His Asn Glu Lys Gly Val Leu Ala Asp Ala Lys Thr Trp
370             375             380

Leu Ser Glu Ser Asn Gly Ile Pro Ser Lys Arg Phe Leu Gly Ile Thr
385             390             395                 400

Gly Ser Pro Lys Phe Asp Ser Tyr Gly Val Asp Phe Gly Trp Gly Lys
                405             410                 415

Pro Ala Lys Phe Asp Ile Thr Ser Ile Asp Tyr Ala Glu Leu Ile Tyr
                420             425                 430

Val Ile Glu Ser Arg Asp Phe Glu Lys Gly Val Glu Gly Val Ser
            435             440             445

Leu Pro Lys Ile His Met Asp Ala Phe Ala Lys Ile Phe Glu Glu Gly
    450             455                 460

Phe Cys Phe Leu Ser
465
```

<210> SEQ ID NO 5
<211> LENGTH: 1587
<212> TYPE: DNA
<213> ORGANISM: Gentiana sp.
<220> FEATURE:
<221> NAME/KEY: CDS
<222> LOCATION: (6)..(1397)

<400> SEQUENCE: 5

```
tcatt atg gag caa atc caa atg gtg aag gtt ctt gaa aaa tgt caa gtt    50
      Met Glu Gln Ile Gln Met Val Lys Val Leu Glu Lys Cys Gln Val
        1               5                  10                  15 aca cca cca tct gac aca aca gat gtc gag tta tca cta tcg gta aca    98
Thr Pro Pro Ser Asp Thr Thr Asp Val Glu Leu Ser Leu Ser Val Thr
             20                  25                  30 ttc ttt gat atc ccc tgg ttg cat ttg tat aag atg cag tcc ctt ctg    146
Phe Phe Asp Ile Pro Trp Leu His Leu Tyr Lys Met Gln Ser Leu Leu
         35                  40                  45 ttt tac gat ttt ccg tat cca aaa acg cgt ttc ttg gac act gtt atc    194
Phe Tyr Asp Phe Pro Tyr Pro Lys Thr Arg Phe Leu Asp Thr Val Ile
     50                  55                  60 cct aat ctt aag gcc tcc ttg tct ctc act cta aaa cac tac ctt ccg    242
Pro Asn Leu Lys Ala Ser Leu Ser Leu Thr Leu Lys His Tyr Leu Pro
 65                  70                  75 ctt agc gga aat ttg tta atg ccc atc aaa tcg ggc aaa atg cca atg    290
Leu Ser Gly Asn Leu Leu Met Pro Ile Lys Ser Gly Lys Met Pro Met
 80                  85                  90                  95 ttt cac tac tct cgt gat gac gga gac tcg ata act ttg atc ttt gcg    338
Phe His Tyr Ser Arg Asp Asp Gly Asp Ser Ile Thr Leu Ile Phe Ala
                100                 105                 110 gag tct gac cag gat ttt gac tac ctt aaa ggt cat cac ctg caa gat    386
Glu Ser Asp Gln Asp Phe Asp Tyr Leu Lys Gly His His Leu Gln Asp
             115                 120                 125
```

```
tcc aat gat ttg cat gcg ctt ttt tat gtt atg cca cgg gtt tta agg    434
Ser Asn Asp Leu His Ala Leu Phe Tyr Val Met Pro Arg Val Leu Arg
        130                 135                 140 acc act caa gac tat aaa gtc atc ccg ctc gta gct gtg caa gta acc    482
Thr Thr Gln Asp Tyr Lys Val Ile Pro Leu Val Ala Val Gln Val Thr
145                 150                 155 gtt ttt cct aac cat ggc att gcc gtg gct ctg acg gca cat cat tca    530
Val Phe Pro Asn His Gly Ile Ala Val Ala Leu Thr Ala His His Ser
160                 165                 170                 175 att gca gat gct aaa agt ttt gta atg ttc atg aat gct tgg gcc tgt    578
Ile Ala Asp Ala Lys Ser Phe Val Met Phe Met Asn Ala Trp Ala Cys
                180                 185                 190 att aac aaa ttt ggg aaa gac aca gac tta ttg tct ggg aat ctt ctt    626
Ile Asn Lys Phe Gly Lys Asp Thr Asp Leu Leu Ser Gly Asn Leu Leu
            195                 200                 205 cca tct ttt gat aga tcg ata atc aaa gat ctg tat ggc cta gag gaa    674
Pro Ser Phe Asp Arg Ser Ile Ile Lys Asp Leu Tyr Gly Leu Glu Glu
        210                 215                 220 aca ttt tgg aac gaa atg caa cat att ctt gac atg ttc tct aga ttt    722
Thr Phe Trp Asn Glu Met Gln His Ile Leu Asp Met Phe Ser Arg Phe
225                 230                 235 gga agc aaa ccc cct cga ttc aac aag gta cga gcc aca tat gtc cta    770
Gly Ser Lys Pro Pro Arg Phe Asn Lys Val Arg Ala Thr Tyr Val Leu
240                 245                 250                 255 tcc cct gtt gaa atc gag aag cta aag aac aaa gta cta aat ctc aga    818
Ser Pro Val Glu Ile Glu Lys Leu Lys Asn Lys Val Leu Asn Leu Arg
                260                 265                 270 gga tct gaa ccg gca ata cgt gta acg acg ttc aca gtg aca tgt gga    866
Gly Ser Glu Pro Ala Ile Arg Val Thr Thr Phe Thr Val Thr Cys Gly
            275                 280                 285 tac ata tgg aca tgc atg gtc aaa tca aaa gat gtc gta tcg aac gac    914
Tyr Ile Trp Thr Cys Met Val Lys Ser Lys Asp Val Val Ser Asn Asp
        290                 295                 300 gaa aat gag ctc gag tac ttc agt ttt aca gcg gat tgc cga ggg ctt    962
Glu Asn Glu Leu Glu Tyr Phe Ser Phe Thr Ala Asp Cys Arg Gly Leu
305                 310                 315 ctg acg ccc ccg tgt ccg cct aac tac ttt ggc aac tgt ctt gcg ccg    1010
Leu Thr Pro Pro Cys Pro Pro Asn Tyr Phe Gly Asn Cys Leu Ala Pro
320                 325                 330                 335 tgc gtt gca aaa gca aca cgt aaa gag tta gtt gga aat aaa ggg ttt    1058
Cys Val Ala Lys Ala Thr Arg Lys Glu Leu Val Gly Asn Lys Gly Phe
                340                 345                 350 ctt gtt gca gtt gca gct att gtg gaa gcc att gaa aag agg gtg cac    1106
Leu Val Ala Val Ala Ala Ile Val Glu Ala Ile Glu Lys Arg Val His
            355                 360                 365 aac gaa aaa ggc gtt ctt gca gat gca aaa act tgg tta tcg gaa tct    1154
Asn Glu Lys Gly Val Leu Ala Asp Ala Lys Thr Trp Leu Ser Glu Ser
        370                 375                 380 aat gga atc cct tca aaa aga ttt ctc ggg att act gga tca cct aag    1202
Asn Gly Ile Pro Ser Lys Arg Phe Leu Gly Ile Thr Gly Ser Pro Lys
385                 390                 395 ttt gat tcg tat ggt gta gat ttt gga tgg gga aag cct gca aaa ttt    1250
Phe Asp Ser Tyr Gly Val Asp Phe Gly Trp Gly Lys Pro Ala Lys Phe
400                 405                 410                 415 gac att acc tct att gat tat gca gaa ttg att tat gtg att gag tcc    1298
Asp Ile Thr Ser Ile Asp Tyr Ala Glu Leu Ile Tyr Val Ile Glu Ser
                420                 425                 430 agg gag ttt gaa aaa ggc gtg gag atc gga gta tca ttg cct aag att    1346
Arg Glu Phe Glu Lys Gly Val Glu Ile Gly Val Ser Leu Pro Lys Ile
            435                 440                 445
```

-continued

```
cat atg gat gca ttt gca aaa atc ttt gaa caa ggt ttt tgc ttt ttg    1394
His Met Asp Ala Phe Ala Lys Ile Phe Glu Gln Gly Phe Cys Phe Leu
        450                 455                 460 tca tagtctcttt aatagaacca aatttgttgc aataaagtac caagtctcta          1447
Ser gtgacactag ttaccaaacc ctactttcga ggtaggagca ccacaacaag gttcaatcac   1507
tacaaggttg aacttcataa attccagagg tcgaatatcc accgttgacc tctgaaaagt   1567
tgaacctcac acctgacatg                                               1587

<210> SEQ ID NO 6
<211> LENGTH: 464
<212> TYPE: PRT
<213> ORGANISM: Gentiana sp.

<400> SEQUENCE: 6

Met Glu Gln Ile Gln Met Val Lys Val Leu Glu Lys Cys Gln Val Thr
  1               5                  10                  15

Pro Pro Ser Asp Thr Thr Asp Val Glu Leu Ser Leu Ser Val Thr Phe
             20                  25                  30

Phe Asp Ile Pro Trp Leu His Leu Tyr Lys Met Gln Ser Leu Leu Phe
         35                  40                  45

Tyr Asp Phe Pro Tyr Pro Lys Thr Arg Phe Leu Asp Thr Val Ile Pro
     50                  55                  60

Asn Leu Lys Ala Ser Leu Ser Leu Thr Leu Lys His Tyr Leu Pro Leu
 65                  70                  75                  80

Ser Gly Asn Leu Leu Met Pro Ile Lys Ser Gly Lys Met Pro Met Phe
                 85                  90                  95

His Tyr Ser Arg Asp Asp Gly Asp Ser Ile Thr Leu Ile Phe Ala Glu
            100                 105                 110

Ser Asp Gln Asp Phe Asp Tyr Leu Lys Gly His His Leu Gln Asp Ser
        115                 120                 125

Asn Asp Leu His Ala Leu Phe Tyr Val Met Pro Arg Val Leu Arg Thr
    130                 135                 140

Thr Gln Asp Tyr Lys Val Ile Pro Leu Val Ala Val Gln Val Thr Val
145                 150                 155                 160

Phe Pro Asn His Gly Ile Ala Val Ala Leu Thr Ala His His Ser Ile
                165                 170                 175

Ala Asp Ala Lys Ser Phe Val Met Phe Met Asn Ala Trp Ala Cys Ile
            180                 185                 190

Asn Lys Phe Gly Lys Asp Thr Asp Leu Leu Ser Gly Asn Leu Leu Pro
        195                 200                 205

Ser Phe Asp Arg Ser Ile Ile Lys Asp Leu Tyr Gly Leu Glu Glu Thr
    210                 215                 220

Phe Trp Asn Glu Met Gln His Ile Leu Asp Met Phe Ser Arg Phe Gly
225                 230                 235                 240

Ser Lys Pro Pro Arg Phe Asn Lys Val Arg Ala Thr Tyr Val Leu Ser
                245                 250                 255

Pro Val Glu Ile Glu Lys Leu Lys Asn Lys Val Leu Asn Leu Arg Gly
            260                 265                 270

Ser Glu Pro Ala Ile Arg Val Thr Thr Phe Thr Val Thr Cys Gly Tyr
        275                 280                 285

Ile Trp Thr Cys Met Val Lys Ser Lys Asp Val Val Ser Asn Asp Glu
    290                 295                 300

Asn Glu Leu Glu Tyr Phe Ser Phe Thr Ala Asp Cys Arg Gly Leu Leu
305                 310                 315                 320
```

```
-continued

Thr Pro Pro Cys Pro Pro Asn Tyr Phe Gly Asn Cys Leu Ala Pro Cys
            325                 330                 335

Val Ala Lys Ala Thr Arg Lys Glu Leu Val Gly Asn Lys Gly Phe Leu
            340                 345                 350

Val Ala Val Ala Ala Ile Val Glu Ala Ile Glu Lys Arg Val His Asn
            355                 360                 365

Glu Lys Gly Val Leu Ala Asp Ala Lys Thr Trp Leu Ser Glu Ser Asn
    370                 375                 380

Gly Ile Pro Ser Lys Arg Phe Leu Gly Ile Thr Gly Ser Pro Lys Phe
385                 390                 395                 400

Asp Ser Tyr Gly Val Asp Phe Gly Trp Gly Lys Pro Ala Lys Phe Asp
            405                 410                 415

Ile Thr Ser Ile Asp Tyr Ala Glu Leu Ile Tyr Val Ile Glu Ser Arg
            420                 425                 430

Glu Phe Glu Lys Gly Val Glu Ile Gly Val Ser Leu Pro Lys Ile His
        435                 440                 445

Met Asp Ala Phe Ala Lys Ile Phe Glu Gln Gly Phe Cys Phe Leu Ser
    450                 455                 460
```